United States Patent
Riccardi et al.

(10) Patent No.: US 9,861,606 B2
(45) Date of Patent: Jan. 9, 2018

(54) THERAPEUTIC FOR TREATING INFLAMMATORY LUNG DISORDERS

(71) Applicants: University College Cardiff Consultants Limited, South Glamorgan (GB); King's College London, London Greater London (GB)

(72) Inventors: Daniela Riccardi, Cardiff South Glamorgan (GB); Paul Jeffrey Kemp, Cardiff South Glamorgan (GB); Christopher John Corrigan, Great Maze Pond London (GB); Jeremy Patrick Thomas Ward, Great Maze Pond London (GB)

(73) Assignees: KING'S COLLEGE LONDON, London (GB); UNIVERSITY COLLEGE CARDIFF CONSULTANTS LIMITED, Cardiff, South Glamorgan (GB)

( * ) Notice: Subject to any disclaimer, the term of this patent is extended or adjusted under 35 U.S.C. 154(b) by 0 days.

(21) Appl. No.: 14/431,382

(22) PCT Filed: Sep. 25, 2013

(86) PCT No.: PCT/GB2013/052505
§ 371 (c)(1),
(2) Date: Mar. 26, 2015

(87) PCT Pub. No.: WO2014/049351
PCT Pub. Date: Apr. 3, 2014

(65) Prior Publication Data
US 2015/0216833 A1 Aug. 6, 2015
US 2016/0271095 A2 Sep. 22, 2016

(30) Foreign Application Priority Data

Sep. 28, 2012 (GB) .................................. 1217330.8

(51) Int. Cl.
*A61K 31/277* (2006.01)
*A61K 45/06* (2006.01)
*A61K 9/00* (2006.01)

(52) U.S. Cl.
CPC .......... *A61K 31/277* (2013.01); *A61K 9/0075* (2013.01); *A61K 9/0078* (2013.01); *A61K 45/06* (2013.01)

(58) Field of Classification Search
CPC ................................................. A61K 31/277
See application file for complete search history.

(56) References Cited

U.S. PATENT DOCUMENTS

| 6,395,919 B1 | 5/2002 | Bhatnagar et al. |
| 6,432,656 B1 | 8/2002 | Del Mar et al. |
| 6,521,667 B1 | 2/2003 | Del Mar et al. |
| 6,750,255 B2 | 6/2004 | Sakai et al. |
| 6,818,660 B2 | 11/2004 | Del Mar et al. |
| 6,864,267 B2 | 3/2005 | Bhatnagar et al. |
| 6,908,935 B2 | 6/2005 | Kelly et al. |
| 6,916,956 B2 | 7/2005 | Shinagawa et al. |
| 6,939,895 B2 | 9/2005 | Sakai et al. |
| 7,084,167 B2 | 8/2006 | Ruat et al. |
| 7,109,238 B2 | 9/2006 | Lago et al. |
| 7,157,498 B2 | 1/2007 | Dauban et al. |
| 7,202,261 B2 | 4/2007 | Del Mar et al. |
| 7,205,322 B2 | 4/2007 | Gungor et al. |
| 7,211,685 B2 | 5/2007 | Shinagawa et al. |
| 7,265,145 B2 | 9/2007 | Dickson et al. |
| 7,829,594 B2 | 11/2010 | Marquis et al. |
| 2002/0099220 A1 | 7/2002 | Del Mar et al. |
| 2004/0009980 A1 | 1/2004 | Bhatnagar et al. |
| 2004/0014723 A1 | 1/2004 | Bhatnagar et al. |
| 2004/0192741 A1 | 9/2004 | Lago et al. |
| 2004/0242602 A1 | 12/2004 | Gungor et al. |
| 2005/0032850 A1 | 2/2005 | Del Mar et al. |

FOREIGN PATENT DOCUMENTS

| EP | 637237 A1 | 2/1995 |
| EP | 724561 A1 | 8/1996 |
| EP | 901459 A1 | 3/1999 |
| EP | 973730 A1 | 1/2000 |
| EP | 1258471 A2 | 11/2002 |
| EP | 1466888 A1 | 10/2004 |
| EP | 1509518 A1 | 3/2005 |
| WO | 9737967 A1 | 10/1997 |
| WO | 9951569 A1 | 4/1998 |
| WO | 0045816 A1 | 8/2000 |
| WO | 200108673 A1 | 2/2001 |
| WO | 0140252 A1 | 6/2001 |
| WO | 2004017908 A2 | 3/2004 |
| WO | 2004041755 A2 | 5/2004 |

(Continued)

OTHER PUBLICATIONS

Yamamura et al. Circ. Res. 2012, vol. 111, pp. 469-481) (Published Online Jun. 22, 2012.*
Chami et al. Compr. Physiol. 2011, vol. 1, No. 4, pp. 1929-1941.*
Davies et al. Am. J. Physiol. Cell Physiol., 2006, vol. 290, pp. C1543-C1551.*
Milara et al. Biochemical Pharmacology, 2010, vol. 80, pp. 236-246.*
Patent Cooperation Treaty, PCT/GB2013/052505, "International Search Report and Written Opinion", dated Sep. 25, 2013, 22 pages.
UK Intellectual Property Office, "Patents Act 1977: Search Report under Section 17(5)" dated Dec. 27, 2012, 5 pages.

*Primary Examiner* — James D. Anderson
(74) *Attorney, Agent, or Firm* — King & Schickli, PLLC

(57) ABSTRACT

A calcium/cation-sensing receptor (CaSR) antagonist to treat an inflammatory lung disorder is described. Methods of treatment including the antagonist, combination therapeutics including the antagonist and at least one other agent, and nebulizers or inhalers including the antagonist are also described.

6 Claims, 15 Drawing Sheets

(56) References Cited

FOREIGN PATENT DOCUMENTS

| | | |
|---|---|---|
| WO | 2004047751 A2 | 6/2004 |
| WO | 2005030746 A1 | 4/2005 |
| WO | 2005030749 A1 | 4/2005 |
| WO | 2005077886 A1 | 8/2005 |
| WO | 2005077892 A1 | 8/2005 |
| WO | 2005108376 A1 | 11/2005 |
| WO | 2004106295 A3 | 12/2005 |
| WO | 2004106296 A3 | 12/2005 |
| WO | 2006041968 A1 | 4/2006 |
| WO | 2006042007 A2 | 4/2006 |
| WO | 2006066070 A2 | 6/2006 |
| WO | 2007044796 A2 | 4/2007 |
| WO | 2007062370 A2 | 5/2007 |
| WO | 2009114098 A2 | 9/2009 |

* cited by examiner

THERAPEUTIC FOR TREATING INFLAMMATORY LUNG DISORDERS

This application is the national stage of international patent application no. PCT/GB2013/052505 filed on Sep. 25, 2013, which in turn claims priority from British Patent Application Ser. No. 1217330.8 filed on Sep. 28, 2012, the disclosures of which are incorporated herein by reference in their entirety.

TECHNICAL FIELD

The invention relates to a therapeutic for treating inflammatory lung disorders particularly, but not exclusively, asthma or chronic obstructive pulmonary disease (COPD); a method of treatment involving said therapeutic; a combination therapeutic comprising said therapeutic and at least one other agent; and a nebuliser or inhaler containing same. The invention has application in the medical and veterinary fields.

BACKGROUND

Inflammatory lung disorders are typically of a chronic nature, they increase morbidity and may, ultimately, cause death. They include a range of diseases including, but not limited to, asthma, bronchitis and chronic obstructive pulmonary disease (COPD).

Of this group, asthma affects 1 in 12 of the population in the UK, with 5.4 million people currently receiving treatment. The UK has one of the highest prevalence of asthma in young adults in Europe and the numbers of children reporting asthmatic symptoms has risen six-fold over the last 30 years. It is estimated that 3 people die each day as a result of asthma. Asthma costs the NHS approximately £1 BN per year and at least one million working days are lost each year due to asthma.

Moreover, while current asthma pharmacotherapy is adequate to control the disease for many patients, a significant number of them do not respond well and continue to suffer from symptoms and from unwanted effects of existing therapies. Indeed, a substantial proportion of the cost of asthma treatment is directed at patients (approximately 10% of the total) whose symptoms are poorly controlled despite aggressive treatment with current therapies.

Thus, there is an urgent need for a better understanding of the pathogenic process in order that new therapeutic agents can be developed which target newly identified molecular mechanisms to improve patients' quality of life and to reduce asthma management costs.

Asthma is characterised by excessive airways narrowing due to bronchospasm, bronchial hyper-responsiveness (BHR), inflammation and airways remodelling. BHR, the phenomenon whereby asthmatic airway smooth muscle is hyper-reactive to a wide variety of specific and non-specific stimuli, is a fundamental pathophysiological feature. Although a comprehensive picture of the major characteristics of BHR exists, the underlying causes are still poorly understood. In asthmatics, plasma concentrations of polycations are markedly increased. Indeed, polycations, such as poly-arginine, poly-L-lysine, spermine and eosinophil-derived cationic proteins (ECPs) are markers for asthma severity, and there is evidence that they may contribute directly to the pathogenesis of the disease. Associations between increases in polycations in the asthmatic airway mucosa and BHR/airway remodelling in asthma have long been apparent and have been ascribed to their positive charge, but the precise molecular mechanisms linking raised polycations to BHR remain unexplained.

However, herein we show for the first time that the extracellular calcium/cation-sensing receptor (CaSR) provides a link between polycations and BHR/airway remodelling in asthma, and so is a key, novel molecular target for asthma treatment.

The CaSR is a pleiotropic, G protein-coupled receptor which plays a fundamental role in mineral ion metabolism (see (1) for recent review). While extracellular $Ca^{2+}$ ($Ca^{2+}_o$) is the physiological ligand for this receptor, CaSR is also activated by many polycations including those implicated in asthma, such as, but not limited to, poly-L-arginine, poly-L-lysine and spermine (2). CaSR signalling results primarily in mobilisation of intracellular $Ca^{2+}$ ($Ca^{2+}_i$) (1), which in the case of airway smooth muscle cells in turn regulates the global contractile response of the cells to a contractile stimulus but also influences the lifespan, migratory and secretory properties of these cells.

We show herein that the CaSR is expressed in human and mouse airway smooth muscle (ASM) cells, where it is activated by polycations, including ECPs, and that these effects are blocked by antagonists such as, but not limited to, negative allosteric modulators of the CaSR, termed "calcilytics". Calcilytics prevent bronchoconstriction induced by polycations and act as mild bronchodilators in mouse intralobular bronchi. Furthermore, we show that, nebulised calcilytics alleviate the BHR induced by polycations or following ovalbumin sensitisation (a common experimental model of asthma) in conscious mice in vivo. Finally, calcilytics reduce inflammatory cell infiltration in two mammalian species of asthma and COPD; the ovalbumin-sensitised/ovalbumin challenged mouse and the lipopolysaccharide-treated guinea pig. Together these data show that the CaSR represents a novel target for inflammatory lung disorders, specifically asthma and COPD.

Notably, calcilytics are safe for human use and already in phase II clinical trials for the treatment of osteoporosis.

Based on the current studies, because of their ability to reduce polycation-induced airway hyper-reactivity and by acting as bronchodilators, we herein teach that locally delivered calcilytics can be used to supress or reverse the functional abnormalities of airway smooth muscle in inflammatory lung disorders and, in particular, asthma and COPD.

SUMMARY

According to a first aspect of the invention there is provided the use of a calcium/cation-sensing receptor (CaSR) antagonist to treat an inflammatory lung disorder.

According to a second aspect of the invention there is provided the use of a calcium/cation-sensing receptor (CaSR) antagonist in the manufacture of a medicament to treat an inflammatory lung disorder.

Reference herein to the term antagonist includes reference to a molecule that binds to said CaSR to inhibit the activity of same such as an agent that binds, reversibly or irreversibly, to the active site of said CaSR or to a molecule that binds to said CaSR to inhibit the activity of same by binding, reversibly or irreversibly, to an allosteric site of said CaSR. The antagonist for use in the invention can be a small molecule or an antagonistic antibody, provided it has the requisite inhibitory activity on the CaSR.

In a preferred embodiment of the invention said antagonists are negative allosteric modulators of said CaSR, termed a "calcilytic".

Calcilytics are well known to those skilled in the art, they are compounds that inhibit, block, or decrease calcium sensing receptor (CaSR) activity. For example the calcilytic may block, either partially or completely, reversibly or irreversibly, the $Ca^{2+}$; mobilizing ability of CaSR; the ability to increase the formation of inositol-1,4,5-triphosphate; or the ability to decrease the formation of cyclic AMP; or the ability to increase the activation of MAPK; or the ability to increase the activation of PI3 kinase; or the ability to increase the activation of Rho kinase. The calcilytic compound for use in the invention can be a small molecule or an antagonistic antibody, provided it has the requisite inhibitory activity on the CaSR.

Calcilytic compounds useful in the present invention include the following: NPS89636 (S)-4'-cyano-3'-3-[2-(4-ethyl-2-fluorophenyl)-1,1-dimethylamino]-2-hydroxy-propoxy-biphenyl-4-carboxylic acid and the structurally unrelated calcilytic, NPS2143 (known as SB262470 and commercially available) as well as those disclosed in U.S. Pat. No. 7,829,594 i.e.

3-{4-Cyano-3-[(R)-2-hydroxy-3-(2-indan-2-yl-1,1-dimethyl-ethylamino)-propoxy]-phenyl}-propionic ethyl ester;

3-{4-Cyano-3-[(R)-2-hydroxy-3-(2-indan-2-yl-1,1-dimethyl-ethylamino)-propoxy]-phenyl}-propionic acid;

3-{4-Cyano-3-[(R)-2-hydroxy-3-(2-indan-2-yl-1,1-dimethyl-ethylamino)-propoxy]-phenyl}-propionic acid isopropyl ester;

3-{4-Cyano-3-[(R)-2-hydroxy-3-(2-indan-2-yl-1,1-dimethyl-ethylamino)-propoxy]-phenyl}-propionic acid 2-ethoxy ethyl ester;

3{4-cyano-3-[(R)-2-hydroxy-3-(2-indan-2-yl-dimethyl-ethylamino)-propoxy]-phenyl}-propionic acid 2-methoxy-1-methyl-ethyl ester;

3-(4-Cyano-3-{(R)-3-[1,1-dimethyl-2-(5,6,7,8-tetrahydro-naphthalen-2-yl)-ethylamino]-2-hydroxy-propoxy}-phenyl)-propionic acid;

3-(4-Cyano-3-{(R)-3-[1,1-dimethyl-2-(5,6,7,8-tetrahydro-naphthalen-2-yl)-ethylamino]-2-hydroxy-propoxy}-phenyl)-propionic acid ethyl ester;

3-(3-Cyano-4-{(R)-3-[1,1-dimethyl-2-(5,6,7,8-tetrahydro-naphthalen-2-yl)-ethylamino]-2-hydroxy-propoxy}-phenyl)-propionic acid;

3-(3-Cyano-4-{(R)-3-[1,1-dimethyl-2-(5,6,7,8-tetrahydro-naphthalen-2-yl)-ethylamino]-2-hydroxy-propoxy}-phenyl)-propionic acid ethyl ester;

3-{4-Cyano-3-[(R)-2-hydroxy-3-(2-indan-5-yl-1,1-dimethyl-ethylamino)-propoxy]-phenyl}-propionic acid; and 3-{4-Cyano-3-[(R)-2-hydroxy-3-(2-indan-5-yl-1,1-dimethyl-ethylamino)-propoxy]-phenyl}-propionate ethyl ester; and pharmaceutically acceptable salts and complexes thereof; and also those disclosed in for example, European Patent and Publications Nos 637,237, 724,561, 901,459, 973,730, 1,258,471, 1,466,888, 1,509,518; International Publication Nos. WO 97/37967, WO 99/51569, WO 01/08673, WO 04/017908, WO 04/041755, WO 04/047751, WO 05/030746, WO 05/030749; WO05077886, WO05077892, WO05108376; WO06041968; WO06042007, WO06066070 WO07062370, WO07044796, WO09114098, U.S. Pat. Nos. 6,395,919, 6,432,656, 6,521,667, 6,750,255, 6,818,660, 6,864,267, 6,908,935, 6,916,956, 6,939,895; 7,084,167; 7,109,238; 7,157,498; 7,202,261; 7,205,322; 7,211,685; 7,265,145, and U.S. Patent Application Publication Nos. 2002/0099220, 2004/0009980, 2004/0014723, 2004/0192741, and 2005/0032850.

Particularly preferred calcilytics are:
NPS89636 or NPS2143 and SB-751689 (Ronacaleret) (GSK); ATF936 (Novartis); SB-423562 and its orally bioavailable precursor SB-423557 (GSK); and NPSP790 and NPSP795, NPS R-568, JTT-305, Calhex 231 (chlorophenyl-carboxamide, also known as compound 7n, and derivatives at substitute at position $N^1$ of $N^1$-arylsulfonyl-$N^2$-[1-(1-naphtyl)ethyl]-trans-1,2-diaminocyclohexanes, compounds 7d, 7e, 7e, 7m), NPS53574 (and substituted 3H-quinazolin-4-ones, compounds 5a,b,d-k,m-t), ATF936 and AXT914 (Novartis).

Specifically, we show herein that the CaSR is expressed in human and mouse airway smooth muscle (ASM) cells, where it is activated by polycations, including ECPs, and that these effects are blocked by negative allosteric modulators of the CaSR, termed "calcilytics".

Furthermore, we show that nebulised calcilytics alleviate the BHR, which is induced by polycations or following ovalbumin sensitisation—an accepted experimental model for asthma studies, in conscious mice, showing that the CaSR represents a novel target for asthma treatment.

Accordingly, in a preferred embodiment of the invention said calcium/cation-sensing receptor (CaSR) antagonist is formulated for administration as an aerosol or mist and, ideally for use with a nebuliser or inhaler, particularly, but not exclusively, a metered dose inhaler or a dry powder inhaler.

The calcilytic, alone or in combination with other therapeutics, can be administered by inhalation in different ways, such as in pressurized metered-dosage inhalers, in dry powder inhalers, in a liquid solution delivered by nebuliser or small volume liquid inhaler, or in a vaporised formulation suitable for inhalation. Although calcilytics have been administered orally for the treatment of other conditions, as with conventional anti-asthma therapy, topical application is likely to carry the most optimal benefit/risk ratio.

Pressurized metered dose inhalers (pMDIs) containing calcilytics, alone or in combination with other therapeutics, with propellants, for example, may be formulated to contain the calcilytics in solution or in dispersion in a propellant, such as HFA 134a or HFA227, alone or in combination with excipients to modify aerosol performance, such as co-solvents (e.g. ethanol, glycerol, polyethylene glycols, propylene glycol), surfactants (e.g. oleic acid) or other excipients such as stabilisers and pH modifiers (e.g. ascorbic acid, sodium edetate, hydrochloric acid). Where the calcilytics are presented as a dispersion in pMDIs then appropriate physical and/or chemical methods may be used to ensure that the aerodynamic particle size upon aerosolisation is appropriate for delivery to the respiratory airways, typically less than 10 μm and preferably less than 5 μm.

Dry powder inhalers (DPIs) containing calcilytics, alone or in combination with other therapeutics, for example, may be formulated to contain the calcilytics as small particles, either alone or in combination with a carrier particle such as lactose or sucrose, to aid aerosolisation. Appropriate physical and/or chemical methods may be used to ensure that the aerodynamic particle size upon aerosolisation from DPIs is appropriate for delivery to the respiratory airways, typically less than 10 μm and preferably less than 5 μm.

Nebulisers and small volume liquid inhaler preparations of calcilytics, alone or in combination with other therapeutics, for example, may be formulated to contain the calcilytics in solution or in dispersion in an aqueous medium, alone or in combination with excipients to modify aerosol performance, such as co-solvents (e.g. ethanol, glycerol, polyethylene glycols, propylene glycol), surfactants (e.g. oleic acid), or other excipients such as stabilisers and pH modifiers (e.g. ascorbic acid, sodium edetate, hydrochloric acid). Where the calcilytics, alone or in combination with other therapeutics, are presented as a dispersion in nebulisers and small volume liquid inhalers then appropriate physical and/or chemical methods may be used to ensure that the aerodynamic particle size upon aerosolisation is appropriate for delivery to the respiratory airways, typically less than 10 µm and preferably less than 5 µm.

Vaporised formulations of calcilytics, alone or in combination with other therapeutics, suitable for inhalation, for example, may be formulated by heating the calcilytics to a high temperature for a short time period, typically less than 1 second, alone or in combination with excipients to modify aerosol performance (e.g. propylene glycol, ethanol). The methods used may ensure that the aerodynamic particle size upon aerosolisation is appropriate for delivery to the respiratory airways, typically less than 10 µm and preferably less than 5 µm.

As mentioned, more preferably, said antagonist, alone or in combination with other therapeutics, may be used for the treatment of the respiratory tract by nasal, bronchial or buccal administration, for example, by the use of aerosols or sprays which can disperse the calcilytic in the form of a powder or in the form of drops of a solution or suspension. Pharmaceutical compositions with powder-dispersing properties usually contain, in addition to the active ingredient, a liquid propellant with a boiling point below room temperature and, if desired, adjuncts, such as liquid or solid nonionic or anionic surfactants and/or diluents. Pharmaceutical compositions in which the pharmacological active ingredient is in solution contain, in addition to this, a suitable propellant, and furthermore, if necessary, an additional solvent and/or a stabiliser. Instead of the propellant, compressed air can also be used, it being possible for this to be produced as required by means of a suitable compression and expansion device.

A pharmaceutical composition in accordance with the invention may be prepared by bringing into association the calcilytic, alone or in combination with other therapeutics, of the invention and a carrier. In general, a formulation is prepared by uniformly and intimately bringing into association the calcilytic, alone or in combination with other therapeutics, with liquid carriers or finely divided solid carriers, or both.

However, in a further preferred embodiment of the invention said calcium/cation-sensing receptor (CaSR) antagonist is formulated for oral administration.

Formulations for oral administration in the present invention may be presented as: discrete units such as capsules, sachets or tablets each containing a predetermined amount of the calcilytic; as a powder or granules; as a solution or a suspension of the active agent in an aqueous liquid or a non-aqueous liquid; or as an oil-in-water liquid emulsion or a water in oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active agent.

Other formulations suitable for oral administration include lozenges comprising the calcilytic, alone or in combination with other therapeutics, in a flavoured base, usually sucrose and acacia or tragacanth; pastilles comprising the calcilyitc in an inert base such as gelatin and glycerin, or sucrose and acacia; and mouthwashes comprising the calcilytic in a suitable liquid carrier.

The oral composition may be prepared by bringing into association the calcilyitc of the invention and the carrier. In general, the formulations are prepared by uniformly and intimately bringing into association the calcilyitc with liquid carriers or finely divided solid carriers or both, and then if necessary shaping the product. The invention extends to a pharmaceutical composition comprising a calcilyitc in conjunction or association with a pharmaceutically or veterinarily acceptable carrier or vehicle for oral administration.

In yet a further preferred embodiment of the invention said calcium/cation-sensing receptor (CaSR) antagonist is used to treat a disease selected from the list comprising: an inflammatory lung disorder, asthma, bronchitis and chronic obstructive pulmonary disease (COPD).

Most preferably said calcium/cation-sensing receptor (CaSR) antagonist, alone or in combination with other therapeutics, is used to treat asthma and/or COPD.

In yet a further preferred aspect of the invention there is provided a method to treat an inflammatory lung disorder comprising administering to an individual said calcium/cation-sensing receptor (CaSR) antagonist.

In the method of the invention, preferably, said calcium/cation-sensing receptor (CaSR) antagonist, alone or in combination with other therapeutics, is formulated for administration as an aerosol or mist and, ideally for use with a nebuliser or inhaler.

In yet a further preferred method of the invention said calcium/cation-sensing receptor (CaSR) antagonist is used to treat a disease selected from the list comprising: an inflammatory lung disorder, asthma, bronchitis and chronic obstructive pulmonary disease (COPD).

Most preferably said calcium/cation-sensing receptor (CaSR) antagonist, alone or in combination with other therapeutics, is used to treat asthma and/or COPD.

According to a yet further aspect of the invention there is provided a combination therapeutic to treat an inflammatory lung disorder comprising a calcium/cation-sensing receptor (CaSR) antagonist as herein described and at least one other therapeutic.

In a preferred embodiment said at least one other therapeutics is an agent to treat an inflammatory lung disorder and, ideally is an anti-asthmatic and/or an anti-COPD.

According to a yet further aspect of the invention there is provided a nebuliser or inhaler containing at least one therapeutic to treat an inflammatory lung disorder wherein said therapeutic is a calcium/cation-sensing receptor (CaSR) antagonist as herein described.

In a preferred embodiment said nebuliser or inhaler contains a combination therapeutic as herein described.

More preferably, said nebuliser or inhaler is used to treat an inflammatory lung disorder selected from the group comprising: asthma, bronchitis and chronic obstructive pulmonary disease (COPD). Ideally, said nebuliser or inhaler is used to treat asthma and/or COPD.

The invention herein described is for use in a mammal, more particularly a human, but the invention also has veterinary application and so use in relation to equine, porcine, canine, feline, ungulate, primate animals or, indeed, in relation to any animal that develops an inflammatory lung disorder.

Throughout the description and claims of this specification, the words "comprise" and "contain" and variations of the words, for example "comprising" and "comprises", mean "including but not limited to" and do not exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

BRIEF DESCRIPTION OF THE DRAWINGS

The invention will now be described, by way of example only, with reference to the following figures and tables wherein.

A. Frozen section from human airway biopsy stained with a polyclonal CaSR antibody (light shade) showing immunoreactivity in both smooth muscle (arrow) and epithelium. L=airway lumen; bar=50 mm. B,C: CaSR immunostaining in a split-open mouse extralolubar bonchus (C) colocalises with calponin (B). D. Transmitted light image showing an interlobular bronchus explant and smooth muscle cells migrating away therefrom. E. An exemplar field of airway smooth muscle (ASM) cells showing CaSR immunoreactivity (light shade). Cells were cultured for 10 days, paraformaldehyde-fixed and identified as smooth muscle using an antibody raised against calponin. F. Human airway smooth muscle cells (HASMCs) were stained with the smooth muscle cell marker (smooth muscle actin) and an anti-CaSR antibody. Magnification: ×20.

Figure 3:
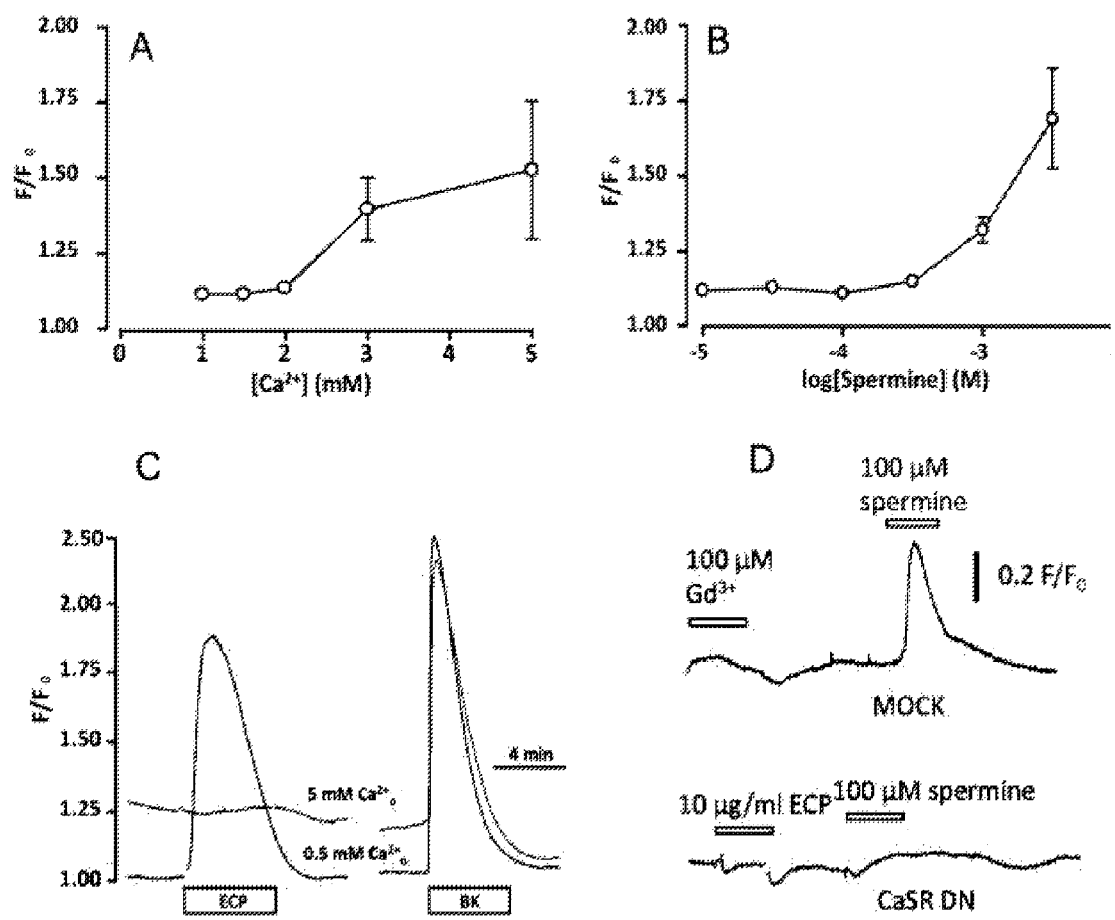

FIG. 3 CaSR can be activated in human airway smooth muscle by $Ca^{2+}_o$ and polycations.

Human ASM cells, loaded with Fura-2 AM, show elevation of $[Ca^{2+}]_i$ ($F/F_0$) when exposed to increased $[Ca^{2+}]_o$ (A, n=7) or spermine (B, n=35; mean±SEM). Panel C shows an exemplar trace of a rise in $[Ca^{2+}]_i$ evoked by 10 μg/ml ECP and by 1 μM bradykinin (BK). In the presence of 5 mM $[Ca^{2+}]_o$ (saturating for CaSR, see A), the response to ECP, but not to BK, is ablated, consistent with CaSR activation by ECP. D), transfection of a "dominant negative" CaSR (CaSR DN) prevents spermine-dependent increase in $[Ca^{2+}]_i$ in human ASM cells, an effect which cannot be seen in MOCK-transfected cells.

Figure 4:
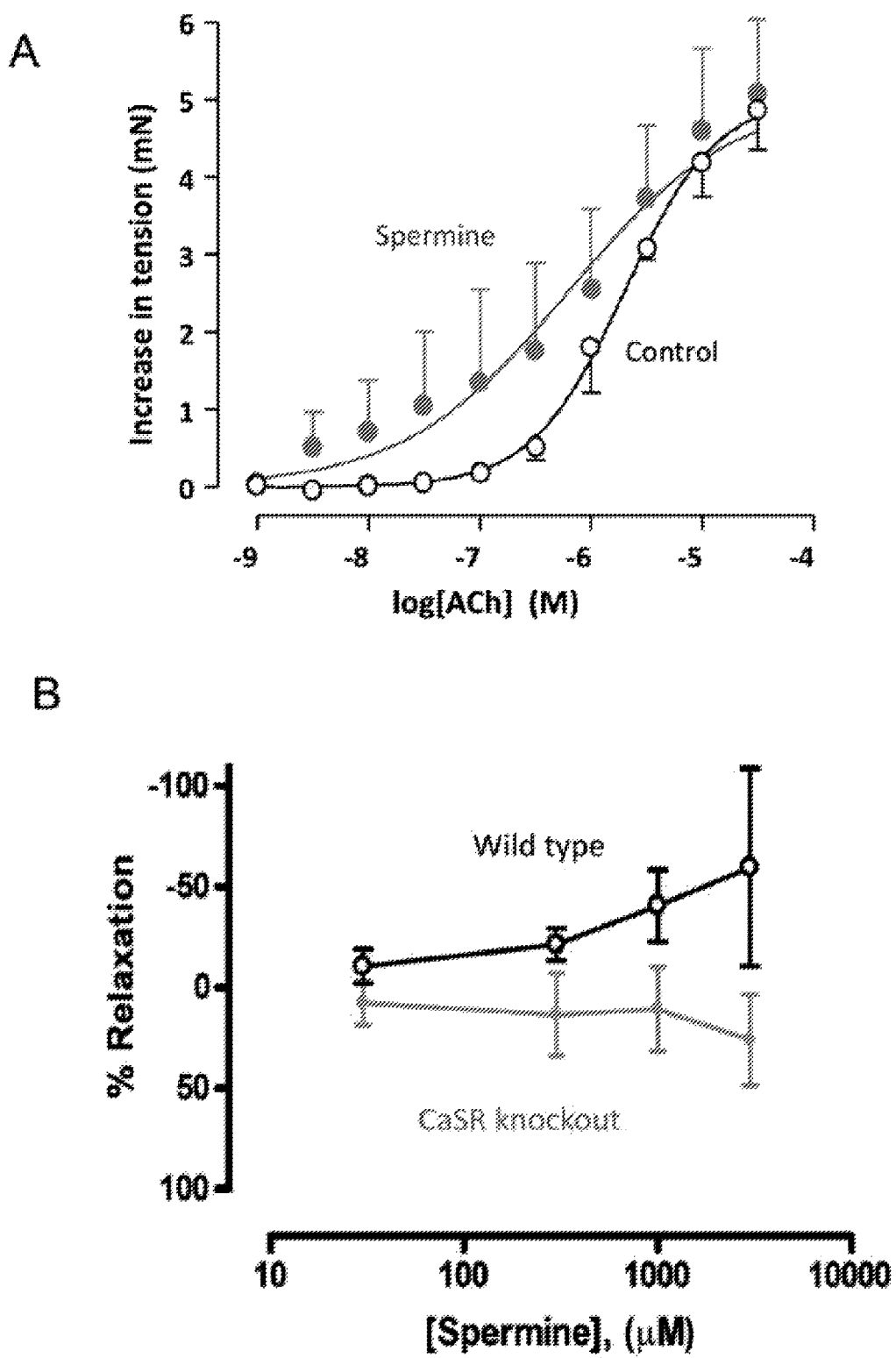

FIG. 4. Spermine enhances ACh-evoked contraction of mouse isolated intralobular bronchi from WT mice, but does not evoke contraction in intralobular bronchi from mice with targeted deletion of the CaSR from smooth muscle cells.

A. Intralobular bronchi were dissected from wild type C57/Bl6 mice (3-4 month of age), mounted upon a wire myograph and bubbled with 95% $O_2$/5% $CO_2$ in the presence of an extracellular solution containing 1 mM $Ca^{2+}_o$. They were then exposed to increasing concentrations of acetylcholine (ACh) in either the absence or presence (15 minute pre-treatment) of 300 μM spermine. Data are mean±SEM, n=3. B. Intralobular bronchi were dissected from wild type (sm22α-Cre$^{-/-}$/floxed-CaSR$^{+/+}$) and CaSR knockout (sm22α-Cre$^{+/+}$/floxed-CaSR$^{+/+}$) mice and were then mounted on a wire myograph, as described in (A). The bronchi were pre-contracted to ~50% of the maximal tone, then increasing concentrations of spermine were added to the bath. Percentage of contraction (upwards deflection from zero of the relaxation curve) or relaxation (downwards deflection from zero of the relaxation curve) were calculated from the tension data. Data are mean±SEM, n=3 per genotype.

Figure 5:
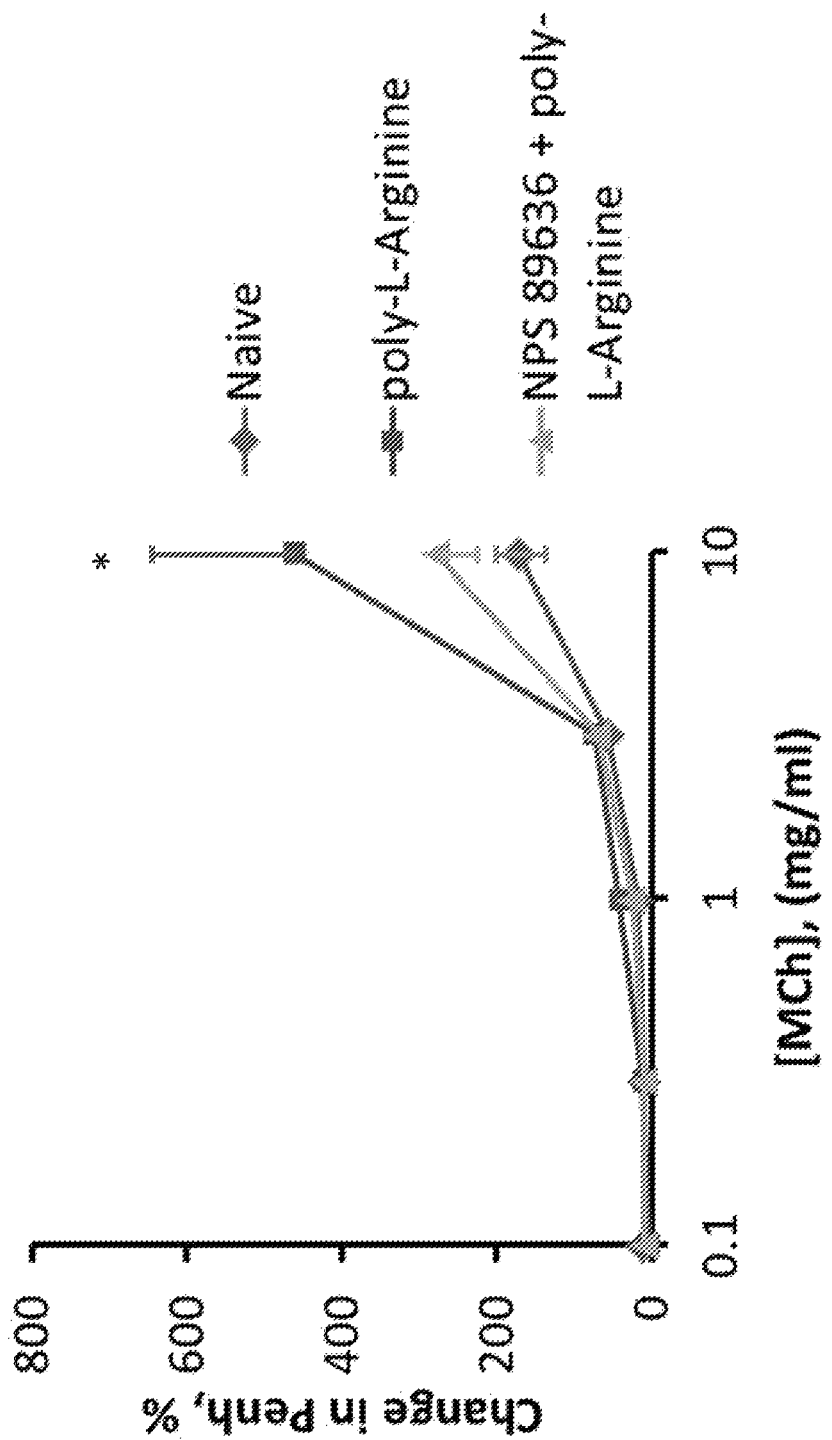

FIG. 5. Calcilytics prevent polycation-evoked BHR in methacholine-challenged mice. Conscious, unrestrained, BalbC mice were equilibrated in a plethysmography chamber for 30 min, then pre-treated for 30 min with either nebulised NPS89636 (3 μM, triangles) or vehicle (0.3% DMSO in saline, diamonds) before being treated with nebulized poly-L-arginine (3 μM, squares) or co-treated with NPS89636 (triangles) for 1 hour. After the treatment, animals were placed in plethysmography chambers (Buxco, USA), allowed to settle for 10 minutes, and then they were challenged with methacholine (MCh, 0.1-10 mg/ml). Responses to methacholine obtained from the animals that have not received any treatments are shown in black symbols. From our previous estimates, ~1-5% of the nebulised drug reaches the lung epithelium. Data are shown as mean changes in Penh±SEM, n=3-6. *significantly different from naïve (p<0.05).

Figure 6:
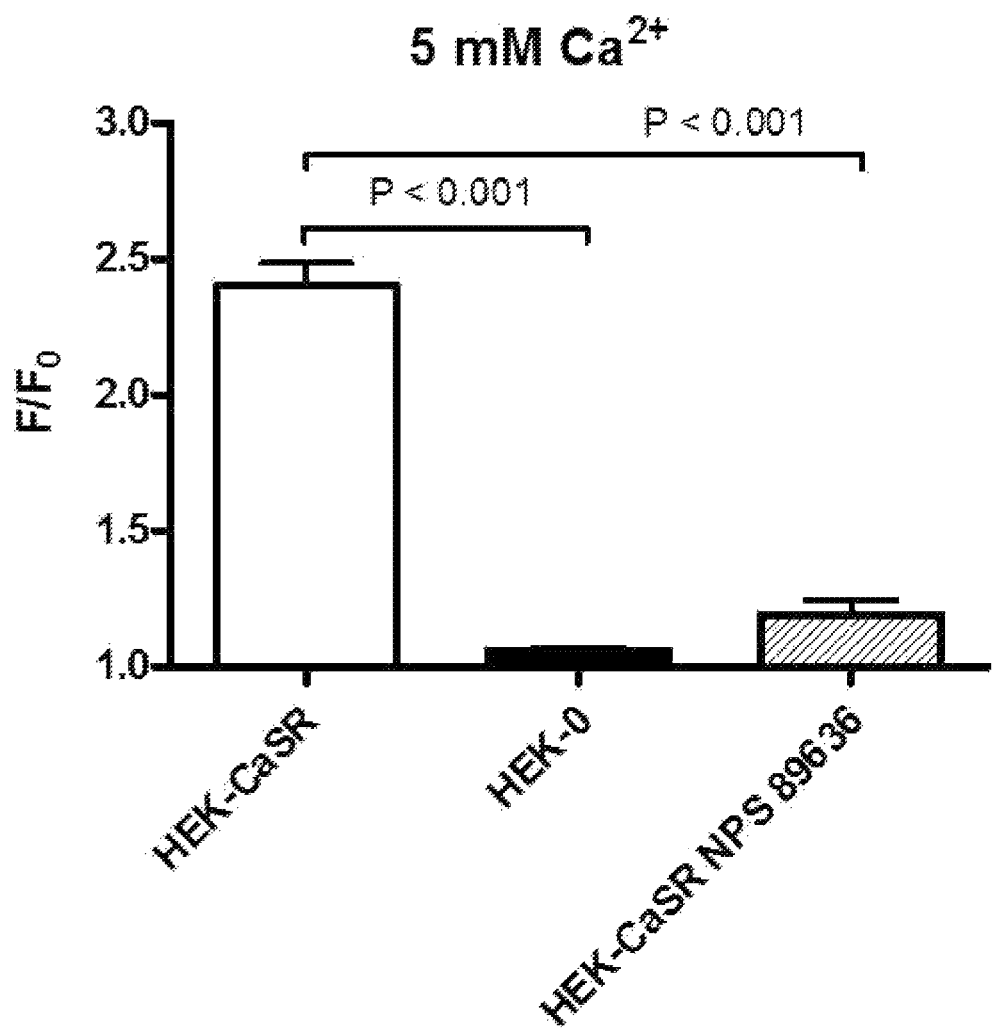

FIG. 6. $Ca^{2+}_o$ activates the CaSR, an effect which can be prevented by the calcilytic NPS89636. HEK293 cells stably expressing the human CaSR (HEK-CaSR) or transfected with empty vector (HEK-0) were loaded with 4 μM fura-2 AM and exposed to 5 mM $Ca^{2+}_o$ in the absence or presence of the calcilytic, NPS89636 (100 nM). Data are from >3 experiments and 121-386 cells. Significant differences are shown above the bars.

Figure 7:
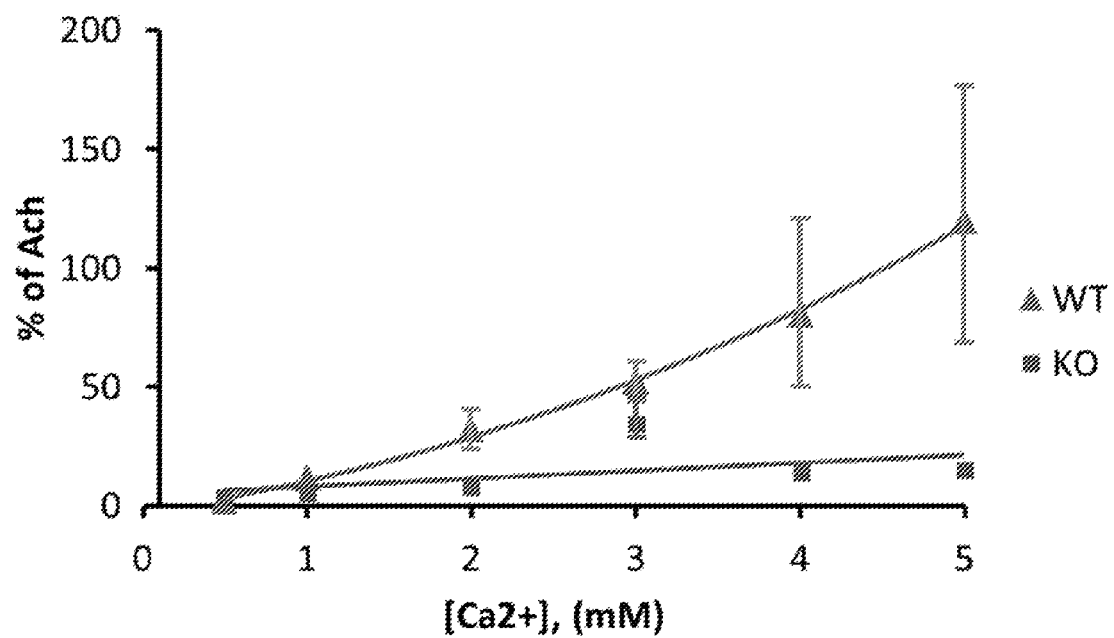

FIG. 7. The CaSR agonist, $Ca^{2+}_o$ causes increases in $[Ca^2]_i$ in mouse primary airway smooth muscle cells (MASMCs) from wild-type mice, but not in MASMCs from mice with targeted deletion of the CaSR from these cells. Intracellular calcium imaging was performed on single cells isolated from mouse interlobular bronchi (passage 2-6) and loaded with 4 micromolar fura-2 AM. WT=cells expressing the CaSR obtained by breeding sm22α Cre⁻ mice with LoxP$^{+/+}$ CaSR mice; KO=cells with CaSR ablation in MASMCs achieved by breeding sm22α Cre⁺ mice with LoxP$^{+/+}$ CaSR mice. Results are expressed as % of the response to the positive control, acetylcholine (3 micromolar ACh). WT: 6-11 cells from 5 experiments; KO: 2-11 cells from 4 experiments. This figure shows functional CaSR ablation in knockout cells, hence the suitability of this mouse model for the studies described in the following figures.

Figure 8:
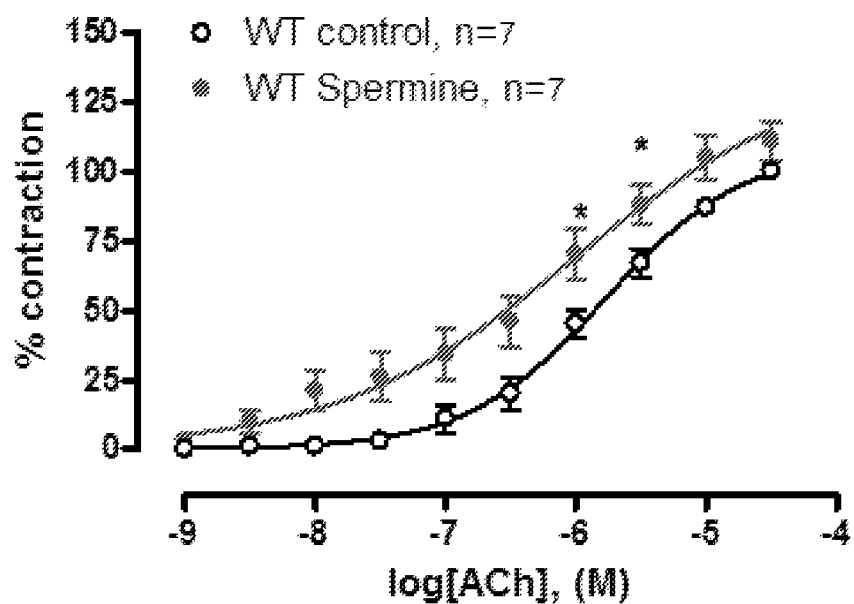
Figure 8:
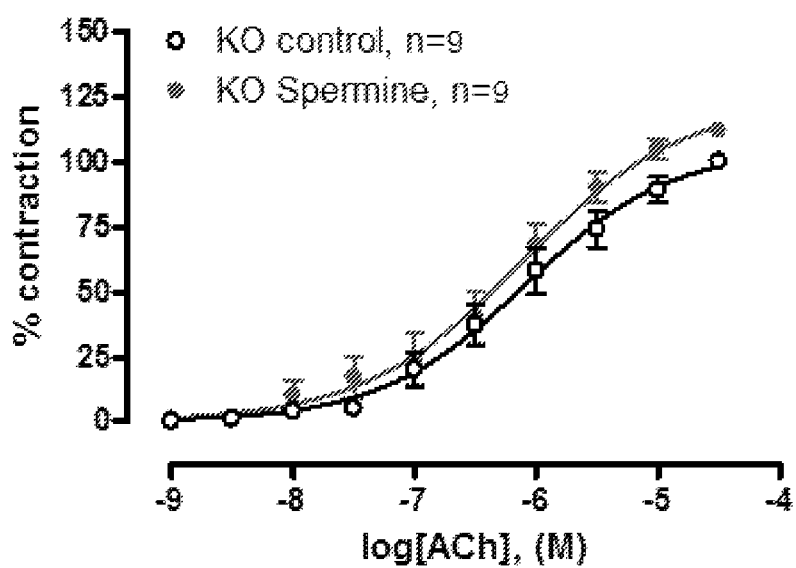

FIG. 8. The CaSR agonist, spermine, enhances ACh-induced airway contraction in intralobular bronchi from WT, but not KO mice. Second/third order intralobular bronchi were dissected from the lung left lobes of WT or KO mice, mounted in small vessel myograph using stainless steel wires (d=40 micrometers) and maintained in a Krebs solution bubbled with 95% $O_2$/5% $CO_2$. Bronchi were left to settle at 37° C. for 30 min, then they were gradually stretched to reach 2 mN of passive tension. After 30 min equilibration time, reactivity of the bronchi was tested by addition of 40 mM KCl to the bath. Bronchi were incubated with spermine for 15 min, and then the broncho-constrictor acetylcholine (ACh, 1 nM-30 micromolar) was cumulatively added to the bath. Data are shown as mean±SEM percentage of contraction normalized to the maximal contraction in control. Asterisks indicate significant differences (*p<0.05).

This figure and the next one show that the CaSR agonists, spermine and Ca (next figure) no longer enhance airway hyper-reactivity in cells lacking their target.

Figure 9:
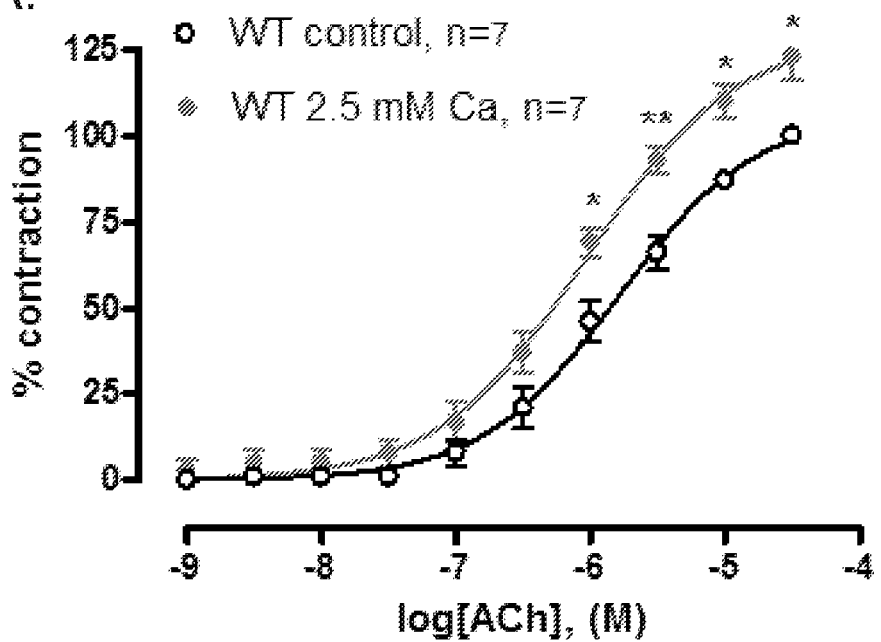
Figure 9:
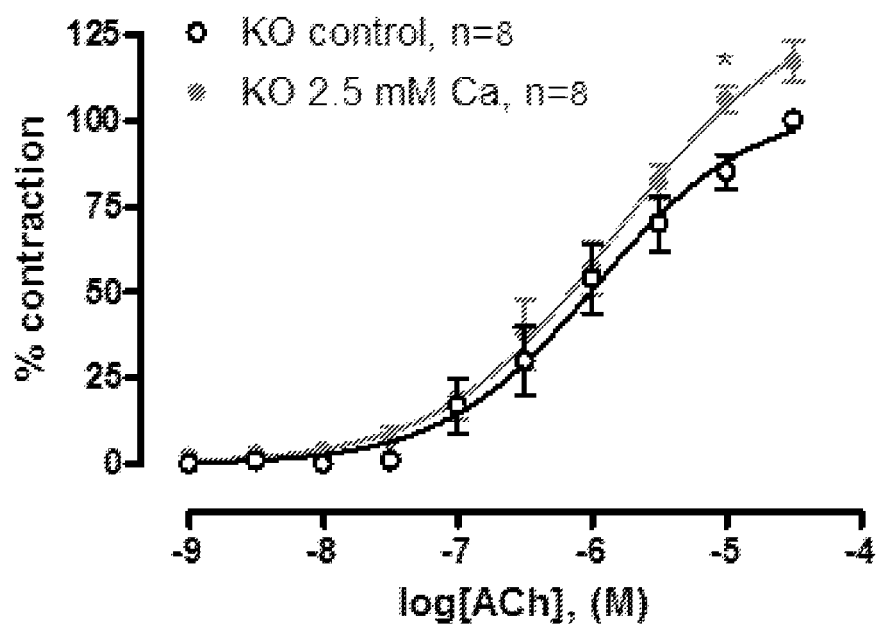

FIG. 9. The CaSR agonist, $Ca^{2+}_o$, enhances ACh-induced airway contraction in intralobular bronchi from WT, but not KO mice. Second/third order intralobular bronchi were dissected from the lung left lobe of WT or CaSR KO mice, mounted on a small vessel wire myograph using stainless steel wires (d=40 micrometers) in a Krebs' solution bubbled with 95% $O_2$/5% $CO_2$. Bronchi were left to settle at 37° C. for 30 min, then gradually stretched to reach 2 mN of passive tension. After 30 min of equilibration time, the reactivity of the bronchi was tested by addition of 40 mM KCl to the bath and were incubated with 2.5 mM $Ca^{2+}_o$ for 15 min, and then acetylcholine (ACh, 1 nM-30 micromolar) was cumulatively added to the bath. Asterisks indicate significant differences (*p<0.05; **p<0.01).

Figure 10:
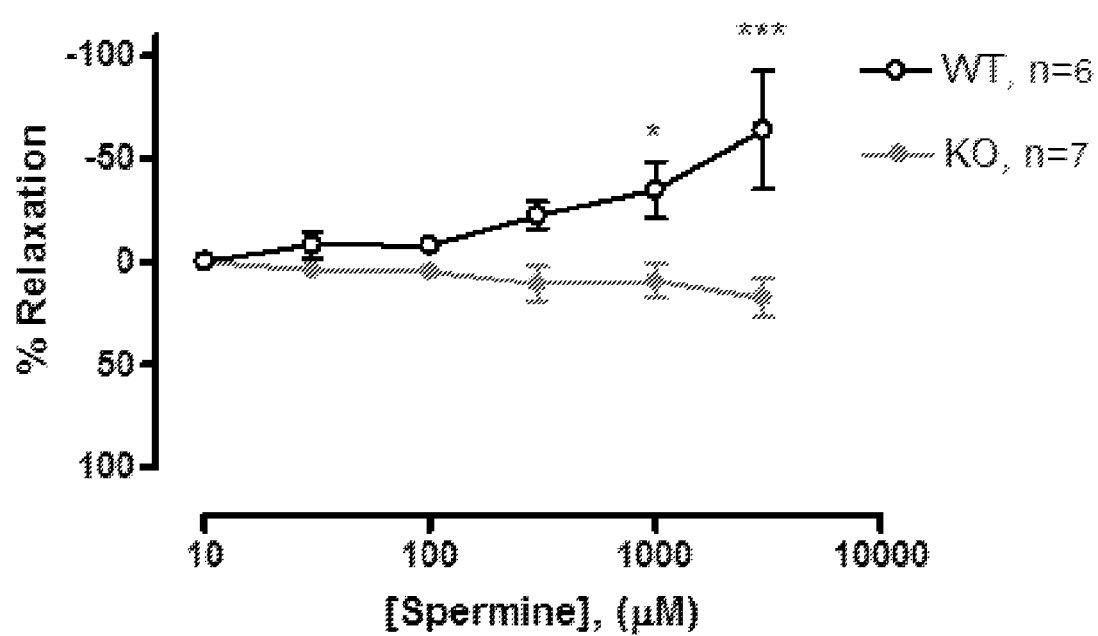

FIG. 10. The CaSR agonist, spermine, enhances bronchial contraction in metacholine-preconstricted intralobular bronchi from WT, but not KO mice. Second/third order intralobular bronchi were dissected from the lung left lobe of WT or CaSR KO mice, mounted in small vessel myograph using stainless steel wires (d=40 micrometers) in a Krebs' solution bubbled with 95% $O_2$/5% $CO_2$. Bronchi were left to settle at 37° C. for 30 min, then gradually stretched to reach 2 mN of passive tension. After 30 min of equilibration time, the reactivity of the bronchi was tested by addition of 40 mM KCl to the bath. Bronchi were precontracted with ACh (1 micromolar) to reach approximately 50% of the maximal tone, after which rising concentrations of spermine (10 micromolar-3 mM) were cumulatively added to the bath. Data are shown as mean±SEM percentage change from baseline, where upwards deflection from zero represents contraction, whilst downwards deflection from zero of the relaxation curve represents relaxation.

Figure 11:
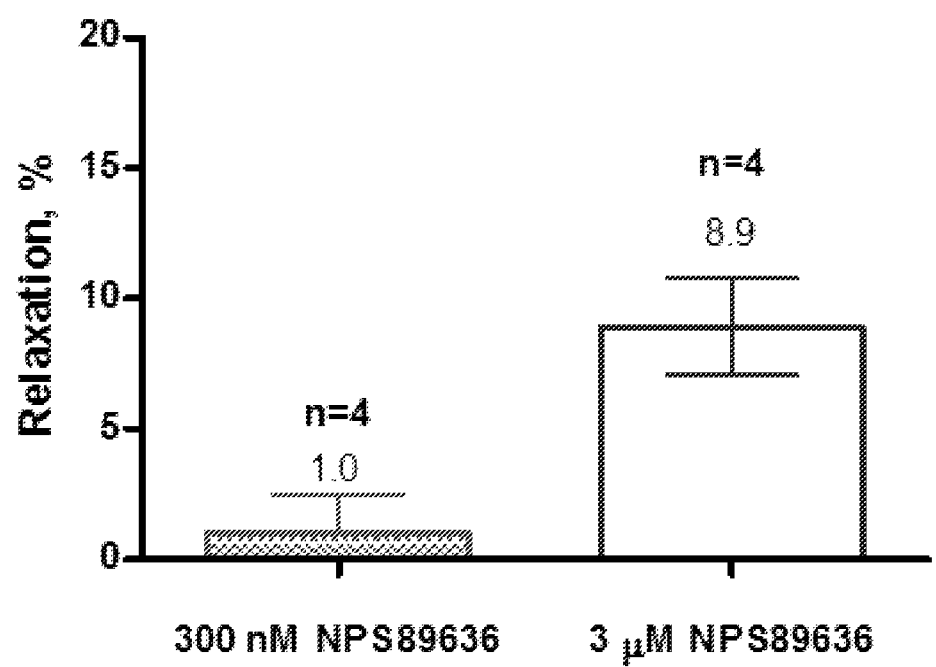

FIG. 11. The calcilytic NPS89636 evokes mild relaxation in acetylcholine-preconstricted intralobular bronchi from WT mice. Second/third order intralobular bronchi were dissected from the lung left lobe of WT or CaSR KO mice, mounted in small vessel myograph. Bronchi were gradually stretched to reach 2 mN of passive tension. After 30 min of equilibration time, the reactivity of the bronchi was tested by addition of 40 mM KCl to the bath. Bronchi were precontracted with ACh (1 micromolar) to reach approximately 50% of the maximal tone, after which NPS89636 (300 nM or 3 micromolar) was added to the bath. Data are shown as mean±SEM percentage change from baseline.

Figure 12:
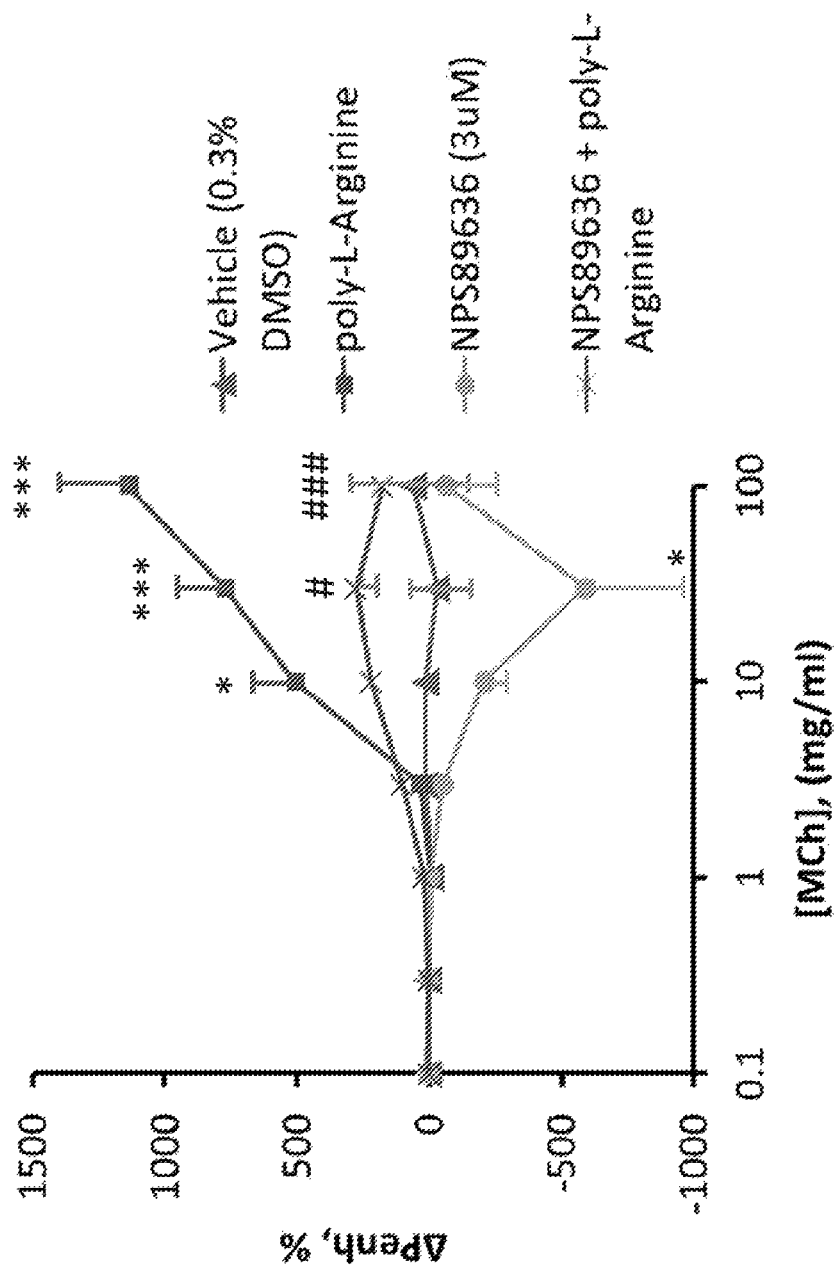

FIG. 12. The calcilytic NPS89636 prevents poly-L-arginine-induced BHR in methacholine challenged mice. Male BalbC mice (~25 g) were purchased from Harlan 1 week before the experimental protocols were performed. The mice were acclimatised to the plethysmography system (Buxco, USA) by being placed therein for 40 min every day for five days prior to the experiment. On the day of the experiment, the body weight of each mouse was recorded and mice were allowed to acclimatise to the chamber for at least 10 min before recordings were made. Then, respiratory activity was recorded for 5 min, to establish baseline value for Penh. Mice were subsequently exposed to increasing concentrations of nebulised methacholine (acetyl-β-methylcholine chloride, MCh, 0.1-100 mg/ml in saline) dissolved in saline solution. Data were recorded for 3 minutes after each aerosol administration. The Penh values at each MCh concentration were averaged and expressed as a proportion of baseline Penh (Penh before treatment).

The next day, mice were treated with nebulised poly-L-arginine (PLA, 3 micromolar), NPS89636 (3 micromolar), poly-L-Arginine+NPS89636 (3 micromolar for both), or vehicle (0.3% DMSO) for 1 hour prior to the lung function measurements, then the methacholine treatment with was repeated as above. The Penh values at each MCh concentration were averaged and expressed as a proportion of that day's baseline Penh (Penh after treatment). Data are presented as percentage change in Penh (delta Penh, %) elicited by each treatment (=Penh after treatment−Penh before treatment×100). MCh: methacholine. N=5 mice per condition. Statistically different from vehicle control * p<0.05 or ** p<0.01, #p<0.05 or ####p<0.001 from treated with poly-L-arginine (two-way ANOVA with Bonferroni post-test).

Figure 13:
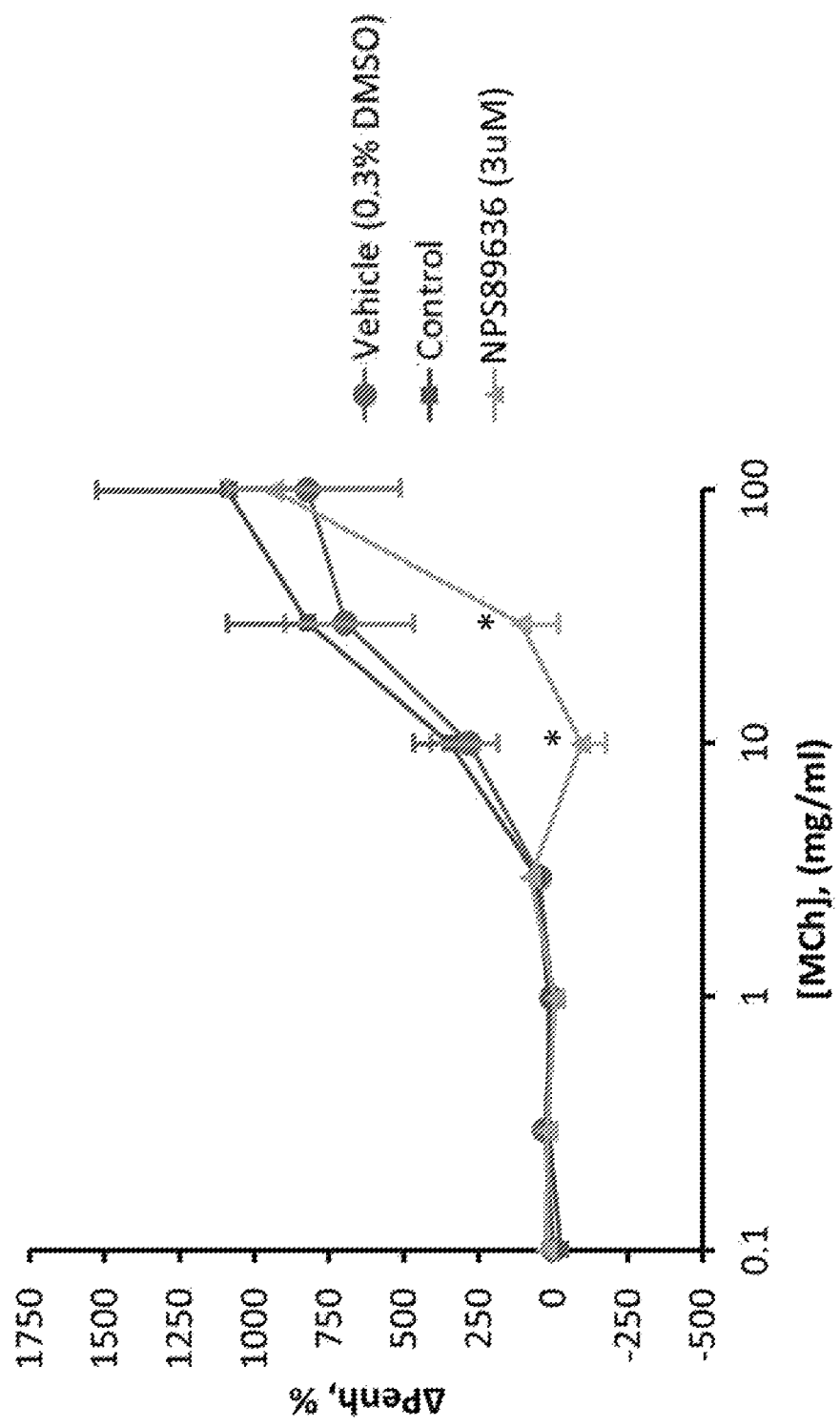

FIG. 13. The calcilytic, NPS89636, prevents ovalbumin-induced BHR in methacholine challenged mice. Mice were sensitised on days 0 and 5 by an i.p. injection of 100 microgram/mouse of ovalbumin (OVA) and 50 mg/mouse aluminium hydroxide in PBS. Fourteen days after the last injection, mice were challenged by inhalation of a 0.5% OVA aerosol in PBS twice on the same day, 4 h apart. Mice were treated with nebulised NPS89636 (3 micromolar) or vehicle (0.3% DMSO) one hour before and three hours after the last OVA exposure. Measurements of BHR following methacholine challenge were taken by plethysmography 24 hours before and after the last OVA inhalation challenge.

Penh was recorded by plethysmography during methacholine challenge, as above (Penh before treatment). 24 hours later, the mice were challenged with 0.5% nebulised OVA (in PBS w/v) in the absence or presence of nebulised NPS89636 (or 0.3% DMSO vehicle) by inhalation. The time-course of this challenge protocol consisted of:

24 hours: OVA for one hour;
27 hours: one of NPS89636 (3 micromolar), DMSO (0.3%) or PBS (control) for one hour;
28 hours: OVA for one hour;
31 hours: one of NPS89636 (3 micromolar), DMSO (0.3%) or PBS (control) for one hour;
32 hours: plethysmography during methacholine challenge as above (Penh after treatment). Data are presented as percentage change in Penh (delta Penh, %) elicited by each treatment (=Penh after treatment−Penh before treatment× 100). N=6 mice per condition. Statistically different from vehicle control * p<0.05.

Figure 14:
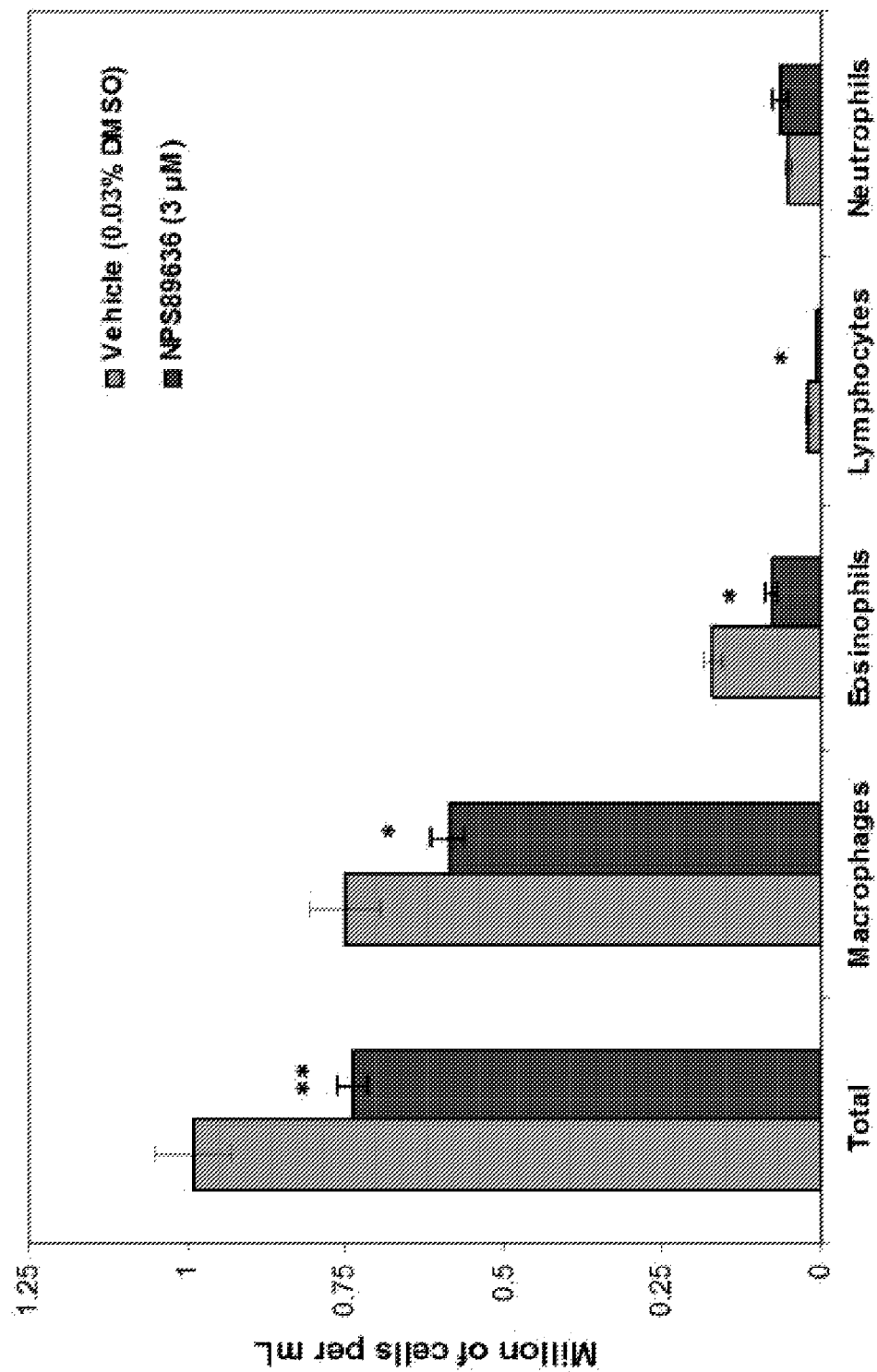

FIG. 14. The calcilytic NPS89636 reduces inflammatory cell infiltration detected in the bronchioalveolar lavage fluid (BALF) from mice sensitized with OVA. 24 hours following the OVA sensitisation and nebulisation protocol described in detail in FIG. 13 in the presence of NS89636 (3 micromolar) or vehicle (0.3% DMSO), mice were killed and the BALF was collected by lavage. Cells from BALF were counted the same day using a haematocytometer. For differential cell count, BALF was concentrated by centrifugation 10 times, 100 microliters of the final solution was applied to a Cytospin 3 Shandon cell smearing system. The slides then were submerged into 1.5% Leisman stain in methanol for 6 min, then briefly washed in water twice, allowed to dry overnight, and the cells counted using 100× oil immersion objective. Data are presented as mean±S.E.M. Significant differences between vehicle and calcilytic are indicated, p<0.05, n=11.

Figure 15:
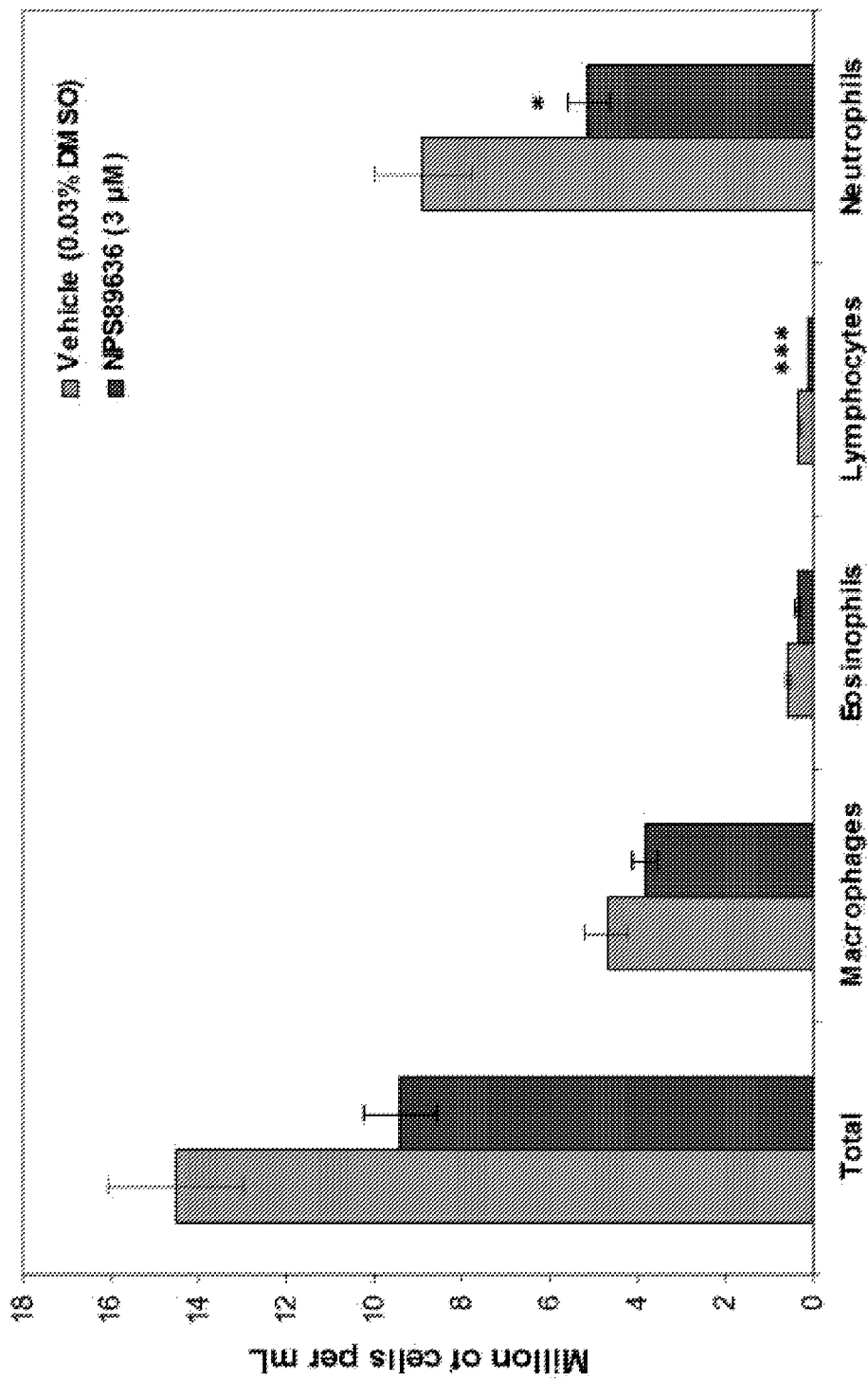

FIG. 15. The calcilytic NPS89636 reduces inflammatory cell infiltration detected in the bronchioalveolar lavage fluid (BALF) from guinea pigs with LPS-induced COPD. Male Dunkin-Hartley guinea pigs (500-550 g) were exposed to 30 micrograms/ml of nebulized lipopolysaccharide (LPS) in saline for 1 hour on alternate days for nine exposures. Animals received nebulised 3 micromolar NPS89636 (or 0.3% DMSO vehicle) for 9 days starting after exposure 5 for 30 min, 30 min before LPS exposure every other day. Animals were killed 24 hours after the ninth exposure (1.5 mL of Euthatal IP) and BALF was collected and cells were counted the same day as described in FIG. 14. Data are presented as mean±S.E.M. Significant differences between vehicle and calcilytic are indicated, p<0.05, n=6.

Table 1. Measurements of Plasma Ionised $Ca^{2+}$ are not Significantly Affected in Balbc Mice 1 h, 4 h or 24 h after Nebulised Calcilytic Treatment.

Reference values for plasma ionised $Ca^{2+}$ in BalbC mice is ~0.8-0.9 mM (http://www.jimmunol.org/content/175/2/917.long#F6)

This table shows that nebulised calcilytic treatment do not affect systemic Calcium levels.

Table 2. Measurements of Plasma Ionised $Ca^{2+}$ are not Significantly Affected in Guinea Pigs 24 h after Nebulised Calcilytic Treatment.

Chemical Structures of Examples of Calcilytics.

NPS 89636

Chemical Name: (S)-4'-cyano-3'-[3-[2-(4-ethyl-2-fluorophenyl)-1,1-dimethylethylamino]-2-hydroxy-propoxy]-biphenyl-4-carboxylic acid hydrochloride LOT NUMBER: PWR-B-039
PHYSICAL APPEARANCE: white solid
STRUCTURE:

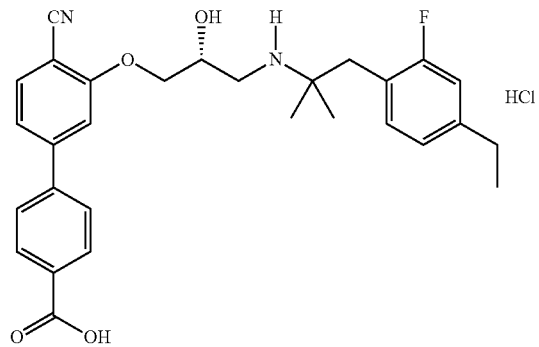 [SMILES: CCc1ccc(CC(C)(C)NC[C@@H](O)COc2cc(-c3ccc(C(=O)O)cc3)ccc2C#N)c(F)c1 ; Cl]

NPS 2143

Chemical Name: 2-Chloro-6-[(2R)-3-[[1,1-dimethyl-2-(2-naphthalenyl)ethyl]amino-2-hydroxy-propoxy]benzonitrile hydrochloride

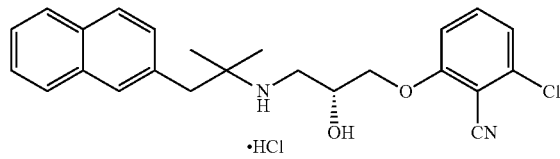 [SMILES: CC(C)(Cc1ccc2ccccc2c1)NC[C@@H](O)COc1cccc(Cl)c1C#N ; Cl]

FW: 445.38
MOLECULAR FORMULA: $C_{24}H_{25}ClNO_2 \cdot HCl$

DESCRIPTION

Materials and Methods
Measurements of Intracellular $Ca^{2+}$ ($Ca^{2+}_i$) Evoked by Polycations in HEK293 Cells Expressing Recombinant Human CaSR and Effects of Calcilytics Upon them HEK293 cells stably expressing the human CaSR (HEK-CaSR) or transfected with an empty vector (HEK-0) were loaded with 4 μM fura-2 AM and exposed to 300 nM poly-L-arginine (Poly-L-Arg), 300 mM-1 mM spermine, 10 μg/ml eosinophil cationic protein (ECP) or 5 mM $Ca^{2+}_o$ in the absence or presence of 100 nM of the calcilytic, NPS89636. The ability of a structurally unrelated calcilytic, NPS2143 (1-10 μM), was also tested on spermine-induced $Ca^{2+}_i$ mobilisation in HEK-CaSR. $Ca^{2+}_i$ release was measured as peak/baseline fluorescence ($F/F_0$). Note that ECP serum concentrations in asthmatic subjects increase with disease severity and are believed to reach ~30 μg/ml.

Expression of the CaSR in Human and Mouse Airway

For human airway, freshly isolated, paraformaldehyde-fixed bronchial biopsies were examined for expression of CaSR in different cell types. Immunohistochemical analysis was performed using our validated anti-CaSR antibodies (3)(FIG. 2A). Mouse intralobular bronchi from C57Bl6 mice were split-opened and paraformaldehyde fixed for 30 min, CaSR and calpain (a marker for ASM cells) immunoreactivites were detected using commercially available antibodies. Images were acquired using an Olympus BX40 microscope. Mouse ASM cells were explanted from fragments of mouse interlobular bronchi dissected from whole mouse lungs (~2 mm per explant). Cells were fixed for 30 min with 2% paraformaldehyde and subsequently immunostained for calpain (a marker for ASM cells, not shown) and for CaSR using commercially available antibodies (4). Human ASM cells from normal and asthmatic volunteers (inclusion criteria as defined elsewhere (5)) were explanted from bronchial biopsies obtained at fibreoptic bronchoscopy from healthy and asthmatic volunteers according to routine protocols established in our laboratories (6, 7). Cultured cells were expanded as necessary and stored for use at early passage (1-5).

Effects of Polycations in Human ASM Cells In Vitro

Once primary human airway smooth muscle cells cell cultures were established at 80-90% confluence using the protocol described above, the endogenous CaSR was activated by exposing these cells to pathophysiologically relevant concentrations of ECPs (1-10 micrograms/ml), spermine (0.1-3 mM) and $Ca^{2+}_o$ (1-5 mM) to determine the effects on intracellular $Ca^{2+}_i$ signalling (using the $Ca^{2+}$-sensitive fluorescent dye, Fura-2). Endogenous CaSR function was down-regulated in human ASM cells by transfecting them with a "dominant negative" CaSR, R185Q, using an Amaxa Nucleofector (8).

Effect of $Ca^{2+}_o$ on ASM Isolated from Mice with Targeted CaSR from Smooth Muscle Cells Mice with CaSR targeted gene ablation from the smooth muscle were generated in our laboratory by breeding sm22α Cre recombinase mice with LoxP CaSR (in which the Lox P site flanking exon 7 of the CaSR)(9). The smooth muscle 22α (sm22α promoter drives Cre recombinase expression almost exclusively in visceral and vascular smooth muscle, and some expression may occur in the cranial suture and in fetal heart (10). These mice have been in Cardiff since January 2010. In our breeding programme we use sm22α-Cre$^{+/+}$/floxed-CaSR$^{+/+}$ (lacking CaSR in smooth muscle) as knockout (KO) mice and sm22α-Cre$^{-/-}$/floxed-CaS$^{+/+}$ (expressing the full-length CaSR in smooth muscle) to act as the wild-type (WT), control mice. Both WT and KO mice are fertile, viable and of a normal lifespan. Mouse ASM cells were explanted from fragments of mouse interlobular bronchi dissected from either WT or KO whole mouse lungs (~2 mm per explant). Passage 2-4 cells were loaded with fura-2 AM and $Ca^{2+}_o$ (1-5 mM)-induced increases in $Ca^{2+}_i$ concentration are presented as % of the maximal response to the positive control, acetylcholine (ACh). WT: 6-11 cells from 5 experiments; KO: 2-11 cells from 4 experiments.

Effect of the CaSR Activators, Spermine or $Ca^{2+}_o$, on Acetylcholine-Dependent Contractile Response in Mouse Intralobular Bronchi Ex Vivo Second/third order intralobular bronchi (approximately 2 mm length) were dissected from the lung left lobes of 5-6 months old wild type (sm22α-Cre$^{-/-}$/floxed-CaSR$^{+/+}$) and CaSR knockout (sm22α-Cre$^{+/+}$/floxed-CaSR$^{+/+}$) mice, mounted in small vessel wire myograph (Danish Myotech) using stainless steel wires (d=40 micrometers) as previously described (11) in a modified Krebs solution contained 1 mM $Ca^{2+}_o$ and bubbled with 95% $O_2$/5% $CO_2$. Bronchi were left to settle at 37° C. for 30 min, then they were gradually stretched to reach 2 mN of passive tension. After 30 min equilibration time, reactivity of the bronchi was tested by addition of 40 mM KCl to the bath. The rings were then exposed to increasing concentrations of acetylcholine (ACh) in either the absence or presence (15 minute pre-treatment) of 300 μM spermine or to a cumulative $Ca^{2+}_o$ of 2.5 mM.

Effect of the Polycation, Spermine, on Bronchi Intralobular Constriction from WT Mice and Mice with Targeted CaSR Deletion from the Smooth Muscle Intralobular bronchi were dissected from wild type (sm22α-Cre$^{-/-}$/floxed-CaSR$^{+/+}$) and CaSR knockout (sm22α-Cre$^{+/+}$/floxed-CaSR$^{+/+}$) mice and were then mounted on a wire myograph, as described previously (12). Increasing concentrations of spermine (10 μM-3 mM) were added to the bath and the contraction (upward deflection from zero) or relaxation (downwards deflection from zero) was calculated from the tension data. WT: n=6; KO: n=7. *p<0.05; **p<0.01.

Effect of the Calcilytic NPS89636 on Mouse Intralobular Bronchi

Second/third order intralobular bronchi were dissected from the lung left lobe of WT or CaSR KO mice, mounted in small vessel wire myograph using stainless steel wires (d=40 micrometers) in a Krebs' solution bubbled with 95% $O_2$/5% $CO_2$. Bronchi were left to settle at 37° C. for 30 min, then gradually stretched to reach 2 mN of passive tension. After 30 min of equilibration time, the reactivity of the bronchi was tested by addition of 40 mM KCl to the bath. Bronchi were precontracted with ACh (1 micromolar) to reach approximately 50% of the maximal tone, after which NPS 89636 (300 nM or 3 micromolar) was added to the bath.

Effect of Polycations and of the Calcilytic NPS89636 on Bronchial Hyper-Reactivity in Unrestrained, Conscious Mice In Vivo Baseline airway hyper-responsiveness was measured by plethysmography. Male BalbC mice (~25 g) were housed in a Perspex chamber and aerosols of CaSR activators (poly-L-arginine) in the presence or absence of the calcilytics NPS89636 were delivered through a Pulmostar nebuliser. Non-invasive measurements of lung function were carried out in unrestrained, conscious mice by barometric plethysmography (Buxco Research Systems) taken before (baseline) and after methacholine challenge. Before each experiment animals were handled and familiarized with the equipment by being placed inside the plethysmography chambers for 40 min every day for 5 days prior to the experiment to reduce stress. Enhanced pause (Penh) (12, 13) was measured as an indicator of airways function in response to inhaled methacholine (1-30 mg/ml) to investigate airways hyper-responsiveness (we have recently shown it to reflect bronchoconstriction evoked by methacholine (14)). All drugs were also tested in naïve animals alone for their ability to influence methacholine challenge. On the day of the experiment, the body weight of each mouse was recorded and mice were allowed to acclimatise to the chamber for at least 10 min before recordings were made. Then, respiratory activity was recorded for 5 min, to establish baseline value for Penh. Mice were subsequently exposed to increasing concentrations of nebulised methacholine (MCh, 0.1-100 mg/ml in saline). Data were recorded for 3 minutes after each aerosol administration. On the next day, mice were treated with nebulised poly-L-arginine (PLA, 3 µM), NPS89636 (3 µM), poly-L-Arginine NPS89636 (3 µM for both), or vehicle (0.3% DMSO) for 1 hour prior to the lung function measurements, then the methacholine treatment was repeated as above. We have previously estimated that for nebulised drugs <10% of the drug actually reaches the lung epithelium (indeed, we believe it to be 1-5%). Therefore we believe the concentrations of the drugs used in the nebulised chamber to be approximately 10-100 fold higher than what we expect to be the effective concentration at the lung epithelium.

The Penh values at each MCh concentration were averaged and expressed as a proportion of that day's baseline Penh (% Penh after treatment). Data are presented as percentage change in Penh (delta Penh, %) elicited by each treatment (=Penh after treatment−Penh before treatment). N=5 mice per condition.

Effect of the Calcilytic NPS89636 on Bronchial Hyper-Reactivity in the Ovalbumin-Sensitised, Ovalbumin-Challenged Unrestrained, Conscious Mouse Model of Asthma In Vivo Male BalbC mice (~25 g) purchased from Harlan and allowed to acclimatise for 1 week prior to experiment. Then, mice were sensitised on day 0 and 5 by an i.p. injection of 100 µg/mouse ovalbumin (OVA) and 50 mg/mouse aluminium hydroxide in PBS. Thirteen days after the last injection, Penh was recorded by plethysmography during methacholine challenge, as described above (Penh before treatment). Next day, the mice were challenged with 0.5% nebulised OVA (in PBS w/v) and nebulised NPS89636 (or 0.03% DMSO vehicle) by inhalation. The time-course of this challenge protocol consisted of:
0 hours: OVA for one hour;
4 hours: one of NPS89636 (3 µM), DMSO (0.03%) or PBS (control) for one hour;
5 hours: OVA for one hour;
9 hours: one of NPS89636 (3 µM), DMSO (0.03%) or PBS (control) for one hour;
29 hours: plethysmography during methacholine challenge as above (Penh after treatment).

At the end of the experiment, bloods were collected via opening the carotid artery. Bloods were allowed to clot for 2-3 hours and spun down at 3000 g for 10 min at 4° C. Collected samples were analysed for measurements of $Ca^{2+}_o$ (performed by the Biochemistry department, University Hospital of Wales).

Bronchoalveolar lavage was performed using three times 1 ml of PBS and the BALF was collected for the quantification of inflammatory cells. The left lung was perfusion-fixed with 4% neutral-buffered formalin for 24 hours while the right lung was kept for RNA/protein analysis. Data are presented as percentage change in Penh (delta Penh, %) elicited by each treatment (=Penh after treatment−Penh before treatment).

Effect of the Calcilytic NPS89636 on Inflammatory Cell Infiltration in LPS-Treated Guinea Pig Model of COPD Male, Dunkin-Hartley guinea pigs were exposed to 30 ug/ml of nebulized lipopolysaccharide (LPS) in saline for 1 hour on alternate days for nine exposures. Animals received drugs/vehicles for 9 days starting after exposure 5: NPS89636 3 µM (or 0.03% DMSO vehicle) for 30 min, 30 min before LPS exposure every other day. Animals were killed 24 hrs after the ninth exposure (1.5 mL of Euthatal ( ) IP) and a bronchoaveolar lavage was performed to determine total and differential cell counts, as described below.

Effect of the Calcilytic NPS 89636 on Inflammatory Cell Infiltration in the BALF of OVA-Sensitised Mice and LPS-Treated Guinea Pigs.

For the asthma model, OVA-sensitized mice were killed by a lethal overdose of sodium pentobarbitone (Euthatal), then using a cannula 1 ml of PBS was instilled into the lungs via an incision in the trachea. The procedure was repeated three times, and 3 ml of the obtained brochoalveolar lavage fluid was spun down and resuspended in 300 microliters PBS. 100 microliters were used for the total cell count and 100 microliters for the cell smear used to perform differential cell count. For the COPD model, the guinea pigs were killed by a lethal overdose of sodium pentobarbitone. An incision into the neck was then made. Subsequently, the trachea was cannulated using an intravenous polypropylene cannula. PBS (1 ml/100 g guinea pig weight) was instilled into the lungs through the cannula and then recovered three minutes later. This process was repeated and the recovered lavage fluid was combined. BALF was diluted 10 times in PBS, 100 microliters of the final solution used for differential cell count.

For the total cell counts 100 microliters of the concentrated BALF from OVA-sensitised mice or 100 microliters of the diluted BALF from guinea pigs were applied to the Cytospin 3 Shandon cell smearing system (using glass slides from Thermo Scientific (BS7011/2; 0.8-1 mm, 76×26 mm) and filter paper from Thermo Scientific (5991022; Shandon filter cards) at 1000 rt/min for 7 minutes. The slides then were immersed into 1.5% Leisman stain in methanol for 6 min, then briefly washed in water twice. The slides were allowed to dry overnight, and the cells were counted using 100× oil immersion objective.

Measurements of Plasma Ionised $Ca^{2+}$

We have shown that the levels of plasma ionised $Ca^{2+}$ are not significantly affected, in either Balbc mice (table 1) or Guinea pigs (Table 2), after nebulised calcilytic treatment. Accordingly, the treatment is not detrimental in mammals.

Statistical Analysis

Unless otherwise stated, data are represented as mean+/− SEM. Statistical analysis was performed using non-paired t test or ANOVA with Bonferroni post-test, and differences were deemed significant for $p<0.05$.

Results

Figure 1:
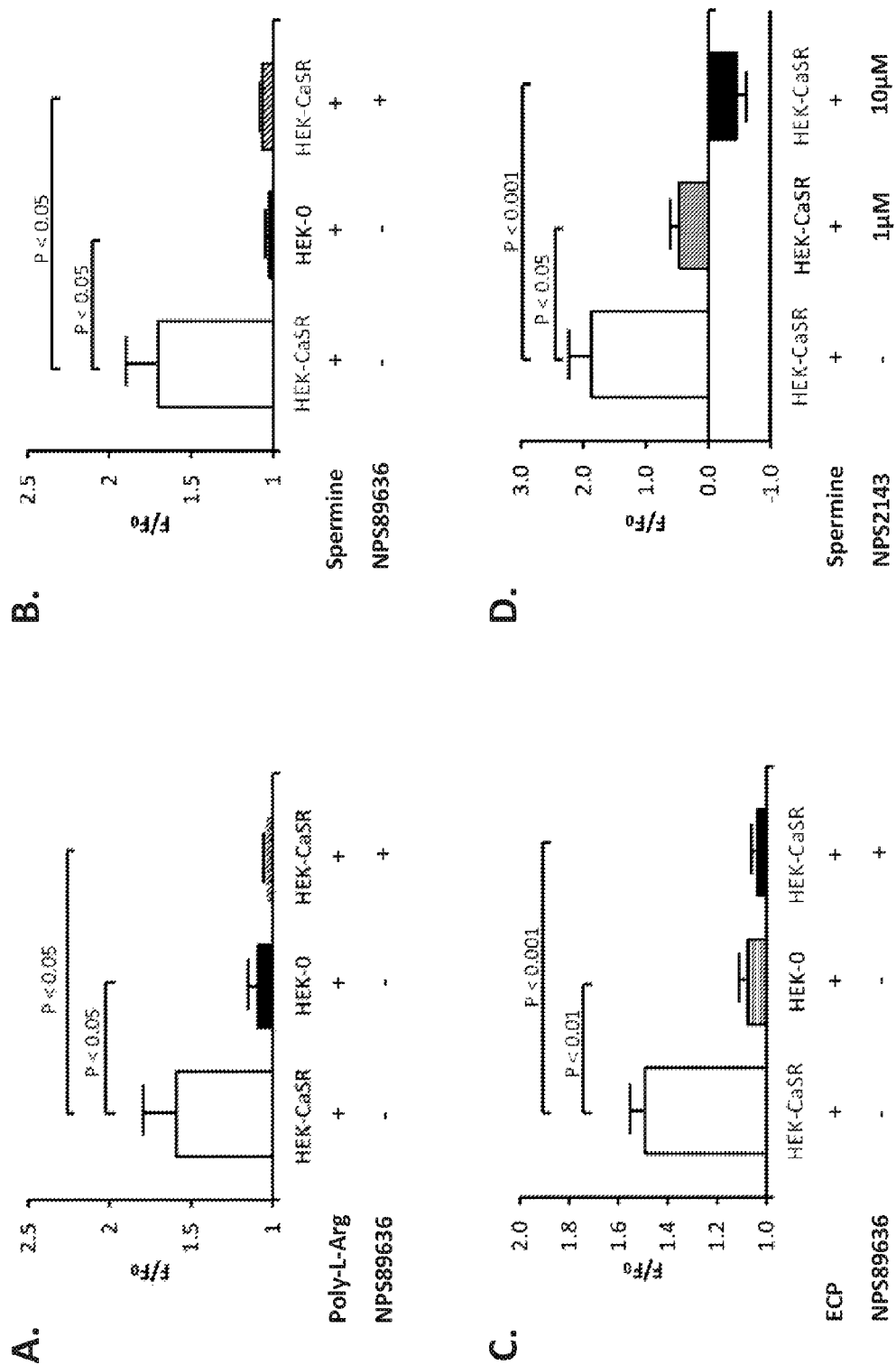
FIG. 1. i) Polycations evoke CaSR-dependent increase in intracellular $Ca^{2+}$; ii) ECPs are novel agonists at the human CaSR; iii) two structurally unrelated calcilytics, NPS89636 and NPS2143, prevent polycation-dependent CaSR activation. HEK293 cells stably expressing the human CaSR (HEK-CaSR) or transfected with empty vector (HEK-0) were loaded with 4 μM fura-2 AM and exposed to 300 nM poly-L-arginine (Poly-L-Arg, A), 1 mM spermine (B) or 10 μg/ml eosinophil cationic protein (ECP, C) in the absence or presence of 100 nM of the calcilytic, NPS89636. The structurally unrelated calcilytic NPS2143 also prevents spermine-induced CaSR activation (D). Responses in mock-transfected cells (HEK-0) were minimal and significantly different from those evoked by agonists. $Ca^{2+}_i$ release (measured as peak/baseline fluorescence emission ratios, $F/F_0$) evoked by all three agonists was significantly reduced by NPS89636. Note that ECP serum concentrations in asthmatic subjects are believed to be ~30 μg/ml. n=121-487 cells, 3-9 experiments. Data are mean±SEM. Where differences are significant, they are shown above the bars.

The CaSR is a pleiotropic, G protein-coupled receptor which plays a fundamental role in mineral ion metabolism (see (1) for recent review). While extracellular $Ca^{2+}$ ($Ca^{2+}_o$) is the physiological ligand for this receptor, CaSR is also activated by many of the polycations including those implicated in asthma, such as poly-L-arginine, poly-L-lysine and spermine (1). Here, we confirm that the human recombinant CaSR, heterologously expressed in HEK293 cells, responds not only to $Ca^{2+}_o$ (FIG. 6), but also to the polycations poly-L-arginine (FIG. 1A) and spermine (FIG. 1B). Furthermore, we provide evidence, for the first time, that ECPs are agonists at the CaSR (FIG. 1C). The specificity of these responses was shown in two ways: firstly, HEK293 cells stably transfected with an empty vector (HEK-0, negative control) did not respond to these agonists and, secondly, the responses to all polycations were completely eliminated by treatment with the calcilytic compound, NPS89636 (FIGS. 1A-C). In addition, a structurally unrelated calcilytic compound, NPS2143, prevented CaSR activation by spermine (FIG. 1D). Together, these data show that polycations, including ECPs, are able to activate CaSR, thereby mobilising $Ca^{2+}_i$. These data also show that calcilytics can prevent the effects of polycations on CaSR activation. As a positive control for these experiments, CaSR stably expressed in HEK293 cells responded to 5 mM $Ca^{2+}_o$ by producing an increase in $Ca^{2+}_i$, an effect which was absent in mock-transfected cells and blocked by NPS89636 (FIG. 6).

Polycations and particularly ECPs have been implicated for many years in contributing significantly to the patho-physiology of BHR and airways remodelling in asthma, but the mechanism has remained obscure. We consider that the mechanism by which they do so depends upon functional expression of CaSR in ASM and/or bronchial epithelial cells.

We have shown herein that CaSR is functionally expressed within the airways of both mice and humans. In bronchial biopsies from human volunteers, CaSR immuno-reactivity is localised within the smooth muscle layer, with additional expression also in the airways epithelium (FIG. 2A). Similar results were also obtained in split-open images of mouse extralobular bronchi immunostained for CaSR and calponin (FIGS. 2B and C). In cells migrating from explanted mouse interlobular bronchi (FIG. 2D) CaSR immunoreactivity is also present (FIG. 2E) and co-localises with calponin (not shown), indicating that the CaSR protein is expressed within mouse ASM cells. Furthermore, CaSR is expressed in primary human ASM (FIG. 2F), Therefore, the CaSR is present in human and mouse airways, both smooth muscle and epithelium.

CaSR activation results primarily in mobilisation of intra-cellular $Ca^{2+}$ ($Ca^{2+}_i$), but CaSR-mediated downstream sig-nalling events also controls control the lifespan, migratory and secretory properties of these cells. Of relevance to asthma and COPD are those pathways which involve acti-vation of PI3K, MAPK, Rho kinase and inhibition of cAMP production. Importantly, mobilisation of $Ca^{2+}_i$ in ASM cells results in changes characteristic of its abnormal function in asthma—BHR, proliferation, migration and secretion of inflammatory and remodelling cytokines.

Figure 2:
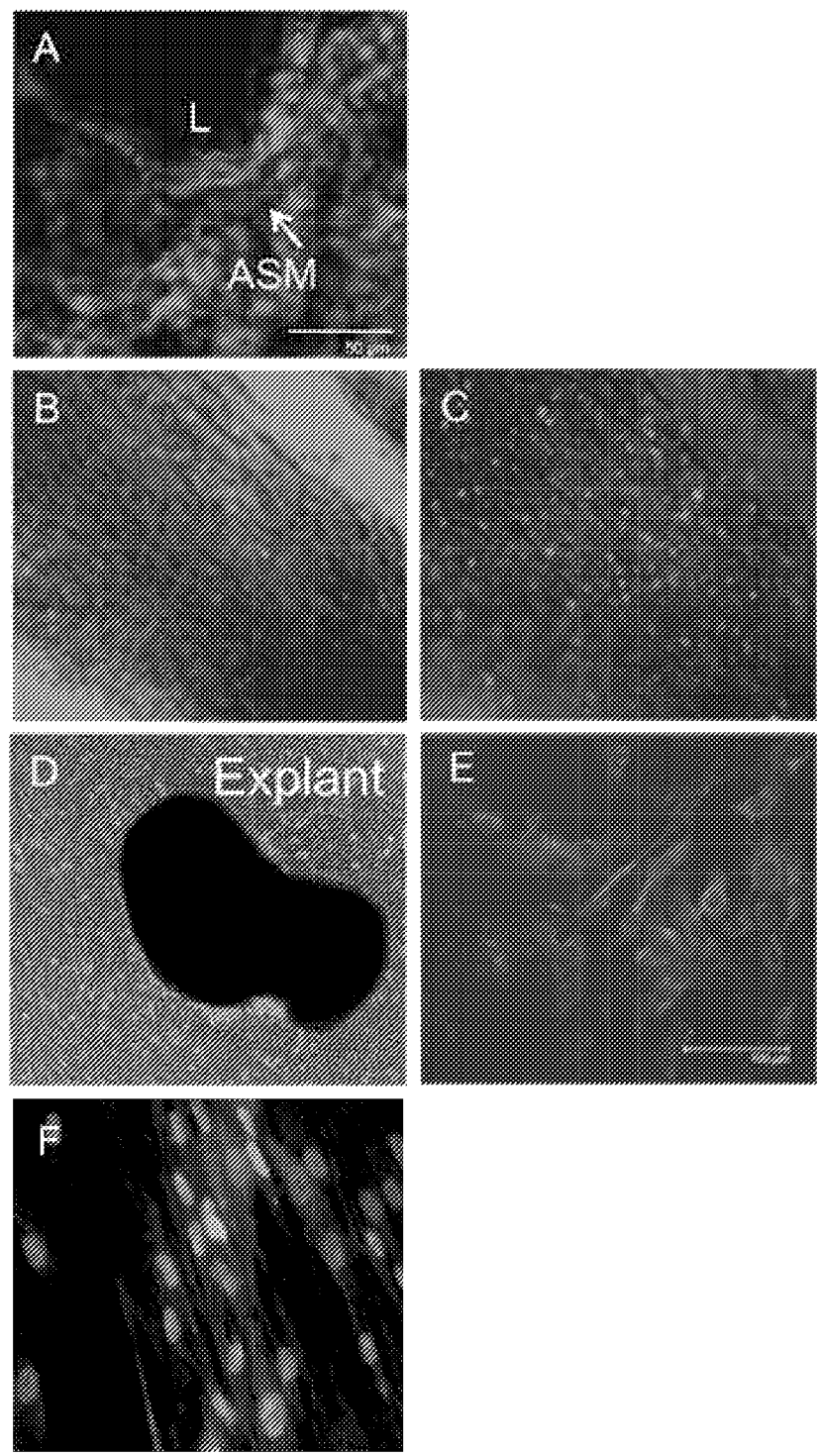
FIG. 2. CaSR immunolocalises to human and mouse airway.

It should be noted that although CaSR is expressed in ASM cells, our initial observations demonstrate that it is also expressed in airway epithelial cells (FIG. 2). In asthma, epithelial cell damage is pathognomonic and the presence of polyamines could directly activate the epithelial CaSR; it is therefore likely that over-activation of the CaSR in human airway epithelium might also play a direct role in the pathogenesis of asthma, especially with regard to airways re-modelling and epithelial permeability.

At the functional level, human ASM cells express the CaSR, as shown by its activation by $Ca^{2+}_o$, spermine and ECPs (FIG. 3). Indeed, $Ca^{2+}_o$ (FIG. 3A) and the polycations spermine (FIG. 3B) and ECPs (FIG. 3C), can all evoke increases in $Ca^{2+}_i$ in human ASM cells. That the CaSR is involved in these responses is evidenced by the following results: i) CaSR activation by ECPs in human ASM cells can be detected in the presence of $Ca^{2+}_o$ concentrations below the threshold of CaSR activation (i.e., 0.5 mM), but it is not observed at a concentration of $Ca^{2+}_o$ which fully saturates the CaSR (i.e., 5 mM, FIG. 3C); ii) this effect by high $Ca^{2+}_o$ does not prevent the ability of an alternative $Ca^{2+}_i$ mobilis-ing agent, bradykinin, to evoke $Ca^{2+}_i$, thereby providing evidence that the $Ca^{2+}_i$ stores are viable; iii) transfection of a "dominant negative" CaSR in human ASM cells prevents CaSR-mediated $Ca^{2+}_i$ mobilisation evoked by the polyca-tions spermine and ECPs (FIG. 3D). Together, these obser-vations strongly suggest that the CaSR is functionally expressed in human ASM cells, where it responds to increas-ing polycation concentrations by inducing $Ca^{2+}_i$ release.

In myography experiments carried out on isolated mouse intralobular bronchi, spermine increases the response to acetylcholine-mediated contraction (FIG. 4A), showing that CaSR activation by this polycation results in a sensitization of the physiological constriction response. Importantly, tar-geted ablation of CaSR from smooth muscle completely ablated the spermine-evoked constrictor response in mouse intralobular bronchi ex viva (FIG. 4B). Together, these observations suggest that CaSR activation by polycations causes bronchoconstriction and, therefore, may directly con-tribute to the symptoms of asthma.

This conclusion is further supported by the data in FIGS. 7-11. In FIG. 7, it is shown that $Ca^{2+}_i$ concentration is increased by the use of the CaSR agonist, $Ca^{2+}_o$, in airway smooth muscle cells isolated from wild-type mice and that this effect was not seen in cells isolated from mice with targeted deletion of CaSR from smooth muscle. Similarly, the CaSR agonists spermine (FIG. 8) and $Ca^{2+}_o$ (FIG. 9), enhance contraction induced by ACh in intralobular bronchi from wild-type mice (FIGS. 8A and 9A), but these effects are not seen in bronchi isolated from the CaSR knock-out mice (FIGS. 8B and 9B). FIG. 10 shows that the CaSR agonist spermine directly evokes bronchoconstriction in wild-type mouse intralobular bronchi but not in the intral-obular bronchi of knock-out mice, indicating that spermine-induced bronchoconstriction was due to CaSR activation. Finally, when a CaSR antagonist, or calcilytic is used, intralobular bronchorelaxation was seen in wild-type mice (FIG. 11). Thus, these data support the hypothesis that CaSR activation by polycations causes bronchoconstriction and even suggest that the CaSR contributes to tonic airway tone since blocking the CaSR with calcilytics evokes a mild bronchodilatation.

To test directly the hypothesis that polycations induce BHR by activating the airway CaSR, we measured bron-choconstriction in conscious, unrestrained mice by whole body plethysmography. Our data indicate that nebulised poly-L-arginine significantly enhanced the response to acute administration of the bronchoconstrictor methacholine (FIG. 5). To provide conclusive evidence for an involvement of the CaSR in mediating polycation-induced BHR, we tested the effects of nebulised administration of calcilytics on poly-L-arginine-induced BHR. Strikingly, our results show that, in mice acutely challenged with methacholine, the poly-L-arginine-induced increase airway reactivity was completely prevented by NPS89636 (FIG. 5).

This conclusion is supported by the data in FIG. 12, which shows that in methacholine challenged mice, the calcilytic NP89636 prevented polycation (poly-L-arginine) induced bronchial BHR.

In order to examine the role of CaSR activation inflam-matory airway disease, two in vivo models were employed. FIG. 12 show data, which were obtained using a standard rodent standard model of asthma, the OVA-sensitised, OVA-challenged mouse. Using this model, we show that NPS89636 completely abolished the methacholine-induced BHR (up to and including 30 mg/ml). Importantly NPS 89636 also reduced the OVA-evoked inflammatory cell infiltration into the lung of these mice (FIG. 14). As a second mammalian model for inflammatory lung disease, we employed an established model of COPD, the LPS-treated guinea pig. When guinea pigs were treated with the calci-lytic NP89636, we observed a reduction in the inflammatory cell infiltration, especially of lymphocytes and neutrophils, in this second mammalian species. These data thus support the hypothesis that the inflammatory response, characterised by cells in the bronchoaveolar lavage fluid, is ameliorated by treatment with a CaSR antagonist. Further, it is notable that an agent that works independently of steroids to reduce inflammation in asthma/COPD is extremely beneficial.

CONCLUSION

These data show that: 1) the CaSR is expressed in human, mouse and guinea pig (i.e. mammalian) airway (smooth muscle and bronchial epithelium); 2) in a mammalian in vitro expression system and in human ASM cells in vitro, ECPs and other polycations evoke an increase in $[Ca^{2+}]_i$ through activation of CaSR, and that this effect can be prevented by calcilytics; 3) spermine and $Ca^{2+}_o$ enhance the contractile response to acetylcholine of mouse intralobular bronchi ex vivo in wild-type mice but not in mice with targeted ablation of CaSR from smooth muscle; 4) The calcilytic NPS89636 produces mild bronchodilatation in mouse intralobular bronchi; 5) in mice acutely challenged with methacholine, poly-L-arginine increases airway hyper-responsiveness in vivo, and this effect is prevented by nebulised calcilytics; 6) in a mouse model of asthma (OVA-sensitised, OVA-challenged) the calcilytic NPS89636 reduces BHR induced by methacholine and inflammatory cell infiltration into the lung, and; 7) in a guinea pig model of COPD (LPS-treatment), the calcilytic NPS89636 also reduces the number of inflammatory cells into the lungs, especially lymphocytes and neutrophils.

Taken together, these observations suggest that inappropriate activation of the CaSR by polycations in the airways of asthmatics, COPD sufferers and mammals having inflammatory lung disorders, evokes BHR and airway remodelling, and so the CaSR constitutes a novel target for the treatment of inflammatory lung disorders including asthma and COPD.

Our project provides a scientific rationale for the use of drugs—calcilytics—already established as safe in humans, either as an alternative therapy, or in combination with current therapies, to alleviate the symptoms of lung disorders such as asthma and/or COPD. Moreover, our new therapy reflects the clinical situation in asthmatics/COPD where the airways smooth muscle is hyper-reactive to a large variety of pharmacological and irritant stimuli. The use of calcilytics to treat asthma and COPD would provide not only an alternative/addition to the existing drugs by being a bronchodilator, but could also target airways hyper-responsiveness improving disease stability and potentially reducing hospital admissions, and airways inflammation and remodelling in the longer term.

REFERENCES

1. D. Riccardi, P. J. Kemp, The calcium-sensing receptor beyond extracellular calcium homeostasis: conception, development, adult physiology, and disease. *Annu Rev Physiol* 74, 271 (2012).
2. E. M. Brown, R. J. Macleod, Extracellular calcium sensing and extracellular calcium signaling. *Physiol Rev.* 81, 239 (2001).
3. B. A. Finney et al., Regulation of mouse lung development by the extracellular calcium-sensing receptor, CaR. *J Physiol* 586, 6007 (2008).
4. B. Finney et al., An exon 5-less splice variant of the extracellular calcium-sensing receptor rescues absence of the full-length receptor in the developing mouse lung. *Exp Lung Res*, (Feb. 26, 2011).
5. K. Mahn et al., Diminished sarco/endoplasmic reticulum Ca2+ ATPase (SERCA) expression contributes to airway remodelling in bronchial asthma. *Proc. Natl. Acad. Sci. U.S.A* 106, 10775 (2009).
6. S. Ge et al., GABA regulates synaptic integration of newly generated neurons in the adult brain. *Nature* 439, 589 (Feb. 2, 2006),
7. C. Fang et al., Resistin-like molecule-beta is a human airway remodelling mediator. *Eur Respir J* 39, 458 (February, 2012).
8. M. U. Alam et al., Calcification is associated with loss of functional calcium-sensing receptor in vascular smooth muscle cells. *Cardiovasc Res* 81, 260 (Feb. 1, 2009).
9. W. Chang, C. Tu, T. H. Chen, D. Bikle, D. Shoback, The extracellular calcium-sensing receptor (CaSR) is a critical modulator of skeletal development. *Sci Signal* 1, ra1 (2008).
10. J. J. Lepore et al., High-efficiency somatic mutagenesis in smooth muscle cells and cardiac myocytes in SM22alpha-Cre transgenic mice. *Genesis* 41, 179 (April, 2005).
11. J. Q. Liu, D. Yang, R. J. Folz, A novel bronchial ring bioassay for the evaluation of small airway smooth muscle function in mice. *Am J Physiol Lung Cell Mol Physiol* 291, L281 (August, 2006).
12. S. Fernandez-Rodriguez, W. R. Ford, K. J. Broadley, E. J. Kidd, Establishing the phenotype in novel acute and chronic murine models of allergic asthma. *Int Immunopharmacol* 8, 756 (May, 2008).
13. E. Hamelmann et al., Noninvasive measurement of airway responsiveness in allergic mice using barometric plethysmography. *Am J Respir Crit Care Med* 156, 766 (September, 1997).
14. S. Fernandez-Rodriguez, K. J. Broadley, W. R. Ford, E. J. Kidd, Increased muscarinic receptor activity of airway smooth muscle isolated from a mouse model of allergic asthma, *Pulm Pharmacol Ther* 23, 300 (August, 2010),

TABLE 1

| Ca++ (mM/L) | Control | Treatment (1 hour) | Treatment (4 hours) | Control (24 hours) | Vehicle (24 hours) | Treatment (24 hours) |
|---|---|---|---|---|---|---|
| BalbC | 0.79 | 0.69 | 0.98 | 1.19 | 1.29 | 1.09 |
| BalbC | 0.61 | 0.88 | 0.94 | 1.07 | 0.87 | 1.1 |
| BalbC | 0.95 | 0.95 | 0.96 | | 1.19 | 0.93 |
| BalbC | | | | | 1.36 | |
| Average | 0.78 | 0.84 | 0.96 | 1.13 | 1.18 | 1.04 |
| Num | 3 | 3 | 3 | 2 | 4 | 3 |
| StDev | 0.170 | 0.135 | 0.020 | 0.085 | 0.217 | 0.095 |
| T-Test | | 0.674 | 0.149 | 0.082 | 0.790 | 0.362 |

TABLE 2

| Ca++ (mM/L) | Vehicle (24 hours) | Treatment (24 hours) |
|---|---|---|
| G.P. | 1.22 | 1.54 |
| G.P. | 1.33 | 1.77 |
| G.P. | 1.61 | 1.58 |
| G.P. | 1.4 | 1.55 |
| G.P. | 1.5 | 1.2 |
| G.P. | 1.5 | 1.55 |
| Average | 1.43 | 1.53 |
| Num | 6 | 6 |
| StDev | 0.139 | 0.184 |
| T-Test | | 0.292 |

The invention claimed is:

1. A method for treating an inflammatory lung disorder in an individual comprising administering to said individual by inhalation an aerosol, a mist, or a powder formulated for penetration into the lung tissue and comprising a calcium/ cation-sensing receptor (CaSR) antagonist to modulate a calcium/cation-sensing receptor expressed in adult lung tissue, wherein said inflammatory lung disorder is selected from the group consisting of asthma, bronchitis and chronic obstructive pulmonary disease (COPD).

2. The method of claim 1, wherein said antagonist is a calcilytic.

3. The method of claim 2, wherein said calcilytic is a small molecule or an antagonistic antibody.

4. The method of claim 2, wherein said calcilytic is selected from the group consisting of NPS89636, NPS2143 (SB-262470), SB-751689 (Ronacaleret), ATF936, SB-423562, SB-423557, NPSP790, NPSP795, NPS R-568, JTT-305, Calhex 231, NPS53574, and AXT914.

5. The method of claim 2, wherein said calcilytic is selected from the group consisting of NPS 89636 (S)-4'-cyano-3'-3-[2-(4-ethyl-2-fluorophenyl)-1,1-dimethyl-amino]-2-hydroxy-propoxy-biphenyl-4-carboxylic acid, NPS2143, 3-{4-Cyano-3-[(R)-2-hydroxy-3-(2-indan-2-yl-1,1-dimethyl-ethylamino)-propoxy]-phenyl}-propionic ethyl ester; 3-{4-Cyano-3-[(R)-2-hydroxy-3-(2-indan-2-yl-1,1-dimethyl-ethylamino)-propoxy]-phenyl}-propionic acid; 3-{4-Cyano-3-[(R)-2-hydroxy-3-(2-indan-2-yl-1,1-dimethyl-ethylamino)-propoxy]-phenyl}-propionic acid isopropyl ester; 3-{4-Cyano-3-[(R)-2-hydroxy-3-(2-indan-2-yl-1,1-dimethyl-ethylamino)-propoxy]-phenyl}-propionic acid 2-ethoxy ethyl ester; 3-{4-cyano-3-[(R)-2-hydroxy-3-(2-indan-2-yl-dimethyl-ethylamino)-propoxy]-phenyl}-propionic acid 2-methoxy-1-methyl-ethyl ester; 3-(4-Cyano-3-{(R)-3-[1,1-dimethyl-2-(5,6,7,8-tetrahydro-naphthalen-2-yl)-ethylamino]-2-hydroxy-propoxy}-phenyl)-propionic acid; 3-(4-Cyano-3-{(R)-3-[1,1-dimethyl-2-(5,6,7,8-tetrahydro-naphthalen-2-yl)-ethylamino]-2-hydroxy-propoxy}-phenyl)-propionic acid ethyl ester; 3-(3-Cyano-4-{(R)-3-[1,1-dimethyl-2-(5,6,7,8-tetrahydro-naphthalen-2-yl)-ethylamino]-2-hydroxy-propoxy}-phenyl)-propionic acid; 3-(3-Cyano-4-{(R)-3-[1,1-dimethyl-2-(5,6,7,8-tetrahydro-naphthalen-2-yl)-ethylamino]-2-hydroxy-propoxy}-phenyl)-propionic acid ethyl ester; 3-{4-Cyano-3-[(R)-2-hydroxy-3-(2-indan-5-yl-1,1-dimethyl-ethylamino)-propoxy]-phenyl}-propionic acid; and 3-{4-Cyano-3-[(R)-2-hydroxy-3-(2-indan-5-yl-1,1-dimethyl-ethylamino)-propoxy]-phenyl}-propionate ethyl ester; and pharmaceutically acceptable salts and complexes thereof.

6. The method of claim 1, wherein said inflammatory lung disorder is asthma or COPD.

\* \* \* \* \*